US007369176B2

(12) United States Patent
Sonnenschein et al.

(10) Patent No.: US 7,369,176 B2
(45) Date of Patent: May 6, 2008

(54) AUTOCLAVABLE IMAGER ASSEMBLY

(75) Inventors: Elazar Sonnenschein, Beer-Sheva (IL);
Binyamin Maly, Moshav Sitriya (IL);
Boris Zarud, Beer-Sheva (IL); Palhaz Shimshilashvili, Beer-Sheva (IL)

(73) Assignee: Medigus Ltd., Omer (IL)

( * ) Notice: Subject to any disclaimer, the term of this patent is extended or adjusted under 35 U.S.C. 154(b) by 840 days.

(21) Appl. No.: 10/631,178

(22) Filed: Jul. 31, 2003

(65) Prior Publication Data
US 2004/0263680 A1 Dec. 30, 2004

(30) Foreign Application Priority Data
Jun. 30, 2003 (IL) .................................... 156715

(51) Int. Cl.
*H04N 5/225* (2006.01)
*A61B 1/04* (2006.01)
*H04N 3/14* (2006.01)

(52) U.S. Cl. .................... 348/374; 348/76; 600/110

(58) Field of Classification Search ................ 348/76, 348/373–376; 600/109, 110, 112
See application file for complete search history.

(56) References Cited

U.S. PATENT DOCUMENTS

| 5,027,218 | A | | 6/1991 | Ueda |
| 5,365,268 | A | * | 11/1994 | Minami ........................ 348/76 |
| 5,754,313 | A | * | 5/1998 | Pelchy et al. ................ 358/473 |
| 5,857,963 | A | | 1/1999 | Pelchy et al. |
| 6,002,425 | A | | 12/1999 | Yamanaka et al. |
| 6,019,719 | A | | 2/2000 | Schulz et al. |
| 6,141,037 | A | * | 10/2000 | Upton et al. ................. 348/65 |
| 6,142,930 | A | * | 11/2000 | Ito et al. ..................... 600/109 |

(Continued)

FOREIGN PATENT DOCUMENTS

EP 0978251 2/2000

(Continued)

OTHER PUBLICATIONS

International Search Report for corresponding PCT appl., mailed Jun. 17, 2004 (7 pages).

(Continued)

*Primary Examiner*—Lin Ye
*Assistant Examiner*—Timothy J Henn
(74) *Attorney, Agent, or Firm*—Roach Brown McCarthy & Gruber, P.C.; Kevin D. McCarthy

(57) ABSTRACT

The invention is an imager assembly for a miniature camera head. The assembly comprises an imaging sensor having conductive leads; an objective lens system placed on top of the sensor; circuitry, mounted beneath the imaging sensor, for driving the sensor and amplifying the electrical signals; and conductive wires electrically linking the internal components of the assembly and for linking the assembly to remote locations. The conductive leads are bent and the circuitry and conductive wires are arranged and mounted such that the dimensions in a plane parallel to the sensor plane of the camera head are approximately equal to or less than the dimensions in the plane of the sensor. The circuitry is capable of delivering signals produced by the imaging sensor for further processing and the components of the imager, except for the imaging surface of the sensor and the objective lens system, are encapsulated by an isolating material.

30 Claims, 16 Drawing Sheets

U.S. PATENT DOCUMENTS

| | | | |
|---|---|---|---|
| 6,547,721 B1 * | 4/2003 | Higuma et al. | 600/133 |
| 6,567,115 B1 * | 5/2003 | Miyashita et al. | 348/76 |
| 6,635,865 B1 * | 10/2003 | Soltyk | 250/239 |
| 2002/0080233 A1 | 6/2002 | Irion et al. | |
| 2002/0180867 A1 | 12/2002 | Adair et al. | |

FOREIGN PATENT DOCUMENTS

| | | |
|---|---|---|
| EP | 1104182 | 5/2001 |
| GB | 2365999 | 1/1998 |
| JP | 11214229 | 2/2001 |
| JP | 2001037713 | 2/2001 |
| JP | 2002131656 | 5/2002 |
| JP | 2002253495 | 9/2002 |
| WO | WO 02/055126 | 7/2002 |

OTHER PUBLICATIONS

Communication relating to the results of the partial international search for PCT/IL03/00633 (a correspoding foreign appl); 3 pages, Feb. 13, 2004.

* cited by examiner

AUTOCLAVABLE IMAGER ASSEMBLY

FIELD OF THE INVENTION

The present invention relates to the field of endoscopy and imaging systems used in minimal access therapy and/or diagnostics. More particularly, the invention relates to arrangements of a miniature camera head allowing compact arrangement of the components of the camera head.

BACKGROUND OF THE INVENTION

The present invention is directed to imager assemblies for miniature camera heads based on solid state sensors e.g., Charged Couple Device (CCD) sensors. These types of cameras are commonly used in imaging systems in minimal access therapy e.g., minimal access surgery, interventional flexible endoscopy, percutaneous interventional radiology, laparoscopy, etc.

Minimal access therapy and/or diagnostics are generally carried out within body cavities and, therefore, the operating field cannot be directly viewed by the person carrying out the operation. For this reason, the ability to carry out such procedures is dependent on the imaging systems that display the images obtained by the camera sensor focused on the scene of the operation.

The imaging systems are usually divided into rigid types of devices (such as laparoscopes) and flexible types of devices (flexible endoscopes). Many of the rigid type devices that are commonly used, known as telescopes, are based on the Hopkins rod-lens system. These devices allow the operator to gain an inner view of the operative field for diagnostics and dissection. The flexible devices that are commonly used are usually based on fiber optic telescopes. These types of flexible endoscopes utilize fiber optics to transmit light into the operative field, and to transfer the image of the operative field to the endoscope eyepiece.

Another type of device that is widely adopted, known as the chip-on-stick technology, is based on optoelectronic instruments. In these devices, an imaging sensor (e.g., CCD) is usually used at the distal end of the telescope or flexible endoscope to record the images produced by an objective lens. Most of the modern miniature cameras that are used in minimal access therapy are of the chip-on-stick variety based on CCD sensors (examples of commercially available devices of this kind are the EndoEYE™ Surgical Videoscopes by Olympus). The optoelectronic systems provide improved image quality and greater light and image sensitivity than the formerly mentioned solutions. However, their performance is affected by the amount of light available in the endoscope, which is dependent upon the size of the illumination means such as the fibers used to transmit the light from a remote source to the operating area, or the Light Emitting Diodes (LEDs) used to illuminate the cavity, e.g., stomach, colon, etc.

The operation of solid state imaging sensors is based on conversion of photons striking the sensor into electron charges (known as the photoelectric effect). The output of the sensor is an electric current, or voltage. The voltage, which is proportional to the number of photons that strike each pixel of the sensor, is amplified by an amplifying device. The amplified signal is usually further processed by converting the voltage signals obtained from the amplifier into equivalent digital signals. Solid-state sensors are utilized to provide images characterized by high-quality and reduced noise levels.

Most chip-on-stick instruments are sensitive to non-chemical sterilization procedures such as autoclaving of the optical components of the imager assembly. This sensitivity results from several causes, one being that the imaging sensor, the objective lens system, and other components of the imager are usually encapsulated utilizing transparent adhesive materials that may lose their transparency as a result of the temperature and pressure involved in the autoclaving process. The loss of transparency is accompanied by a substantial deterioration of the optical qualities of the imager. Another cause of the sensitivity is problems caused by leakage resulting from the pressure of the steam involved in autoclaving.

Additionally, signal distortions result, during medical and industrial procedures, when the environment is hot in comparison to the room temperature or due to residual heat after the autoclaving procedure. It is possible that some of these problems can be overcome by arranging the imager components in a spaced construction utilizing a dedicated enclosure and fastening elements, as described in U.S. Pat. No. 6,019,719. However, although this spaced construction resolves the autoclaving drawbacks discussed above, it also substantially enlarges the imager dimensions. Thus it is not a viable solution when it is necessary to include miniature electrical circuitry in the vicinity of the imaging sensor, as is the case in applications utilizing relatively small imaging sensors.

There is an ongoing effort to reduce the dimensions of the camera heads used in optoelectronic instruments, in order to provide improved penetration and access to bodily organs, e.g., to the lower layer of the lung or deep into the kidney, brain, etc. One of the difficulties that must be solved in designing increasingly smaller camera heads is that the density of photons received by the imaging sensor becomes limited by the sensor's small dimensions. Additionally, the amount of light illuminating the scene is small since the source of illumination (e.g., fiber, LED, or the like) must also be kept very small. Therefore, the signal received from the imaging sensor has to be amplified requiring the use of additional electrical components that are preferably mounted in the vicinity of the imaging sensor. Use of these additional electrical components increases the complexity of the camera heads and multiplies the difficulties in creating miniature and autoclavable imager designs.

An imager assembly is described in U.S. Pat. No. 5,857, 963, in which the imaging sensor is mounted on a T-shaped support member 300a, as shown in FIG. 3A. In this assembly the imaging sensor 301 is located in a recess formed on the horizontal member 300b. Circuitry components 313a to 313d, for driving the imaging sensor 301, are mounted on the vertical member 300a. This assembly is beneficial in applications utilizing imaging sensors of relatively large dimensions (e.g., ⅛" or ¼" CCDs), wherein all the electrical components 313a to 313d can be compactly arranged on the vertical member 300a without affecting the overall dimensions of the imager assembly.

However, if the imaging sensor used is of relatively small dimensions (e.g., ~2×2 mm or less), the imager assembly design requires careful consideration of the lengths of the electrical components 313a to 313d. It can be seen that the dimensions of the imager assembly shown in FIG. 3A (in a plane parallel to the plane of the sensor) can be reduced by mounting the imaging sensor on a horizontal member which has same, or smaller, dimensions as those of the imaging sensor 301, as shown in FIG. 3B. Since the lengths of the electrical components 313a to 313d are typically about 1 mm, in applications utilizing imaging sensors approximately equal to, or smaller than, 2×2 mm, the edges of the electrical components will project beyond the virtual edges e1 and e2 defined by the dimensions in the plane of the imaging sensor 301. In this case, the dimensions in the plane parallel to the plane of the sensor of the imager assembly are determined by the thickness of the vertical member 300a and the length of the electrical components 313a to 313d.

A different imager assembly is described in U.S. Pat. No. 5,754,313. As shown in FIG. 4A, in this assembly two vertical members, 303a and 303b, are used to support a horizontal member 302 on which the imaging sensor 301 is mounted. The electrical components 313a to 313d are mounted on the inner side of the vertical members 303. This assembly suffers from the same drawbacks described hereinabove with regard to FIG. 3A and it is mainly suitable in applications utilizing relatively large imaging sensors.

The assembly shown in FIG. 4B illustrates how these drawbacks could be solved when the imaging sensor 301 utilized is of relatively small dimensions (approximately equal to, or smaller than 2×2 mm). In the assembly shown in FIG. 4B, the electrical components 313a to 313d are arranged in opposite directions on the inner sides of the vertical members 303. But since some of the components cannot be located directly opposite other components, because their combined length exceeds the limited space available, the electrical components must be mounted in a spaced apart arrangement as shown in FIG. 4B. In the arrangement shown in FIG. 4B the width of the imager corresponds to the dimensions of the imager sensor; however to achieve this result the length of the vertical members 303 must be increased over that of the design shown in FIG. 4A in order to provide the required space for all of the electrical components.

In the imager assembly described in U.S. Pat. No. 6,142,930 a different design approach is used. In this assembly the electrical components are mounted on a circuit board positioned behind the imaging sensor. Since this imager is designed to be installed in a shielded pipe, reinforcing plates are required to support the imager, and the imaging sensor leads are bent into an L-shape in order to connect them to the bottom side of the circuit board. This design requires less space than the abovementioned designs, however it is far from optimal as far as miniaturization is concerned and must be improved upon to accommodate the required circuitry and imaging sensors of relatively small dimensions (e.g., to fit into a package having a cross-section of less than or approximately equal to 2×2 mm and having a very short length). The design is not optimal since the CCD is supported by an external housing; the electrical components are placed on a plate within the housing, spaced apart from the CCD; and because of the presence of a separate reinforcement plate for a flexible circuit board.

A similar approach is also used in patent application JP 2001037713A2, wherein two parallel Printed Circuit Boards (PCB's) situated behind the imaging sensor are used for mounting the electrical components. The approach does not make optimal use of the space behind the CCD and therefore the overall dimensions of the imager are not suitable for assemblies using very small imaging sensors (less than or approximately equal to 2×2 mm).

The methods described above do not provide a satisfactory solution to the problem of minimizing the dimensions of imager assemblies that comprise an imaging sensor of relatively small dimensions. The prior art assemblies also fail to provide miniature imager assemblies utilizing very small imaging sensors that maintain their optical qualities even after being repeatedly sterilized utilizing autoclaving procedures.

It is an object of the present invention to provide an imager assembly utilizing an imaging sensor of relatively small dimensions having efficient and minimal packaging confined by the dimensions, of the imaging sensor.

It is another object of the present invention to provide an imager assembly that can be efficiently sterilized utilizing autoclaving sterilization procedures.

It is a further object of the present invention to provide an imager assembly having minimal dimensions and improved flexibility enabling it to be utilized with very small diameter endoscopes.

It is a still further object of the present invention to provide an imager assembly and related electronics comprising means to overcome problems caused by the miniaturization process, e.g., means of reducing the electrical noise, flicker, etc.

It is yet another object of the present invention to provide an imager assembly utilizing an imaging sensor of relatively small dimensions having efficient and minimal packaging and providing high quality and stable images under conditions of relatively low levels of illumination.

Other objects and advantages of the invention will become apparent as the description proceeds.

SUMMARY OF THE INVENTION

In a first aspect the present invention is directed towards an imager assembly for a miniature camera head. The basic preferred embodiment of the imager assembly of the invention comprises the following components:

a) an imaging sensor having conductive leads emanating from two opposite sides of the sensor, for outputting and/or inputting electric signals and/or power;

b) an objective lens system placed on top of the sensor;

c) circuitry, mounted beneath the imaging sensor, for driving the sensor and amplifying the electrical signals; the components of the circuitry are electrically linked, according to the circuit requirements, to each other and to the sensor leads by conductive wires;

d) conductive wires electrically linked to the circuitry and to the leads of the imaging sensor for conducting electrical signals between the electrical circuitry and a remote location; and e) conductive wires electrically linked to the circuitry and to the leads of the imaging sensor to provide them with electrical power from an external power supply.

The conductive leads are bent and the circuitry and the conductive wires are arranged and mounted such that the dimensions of the camera head in the plane parallel to the sensor plane ("sensor plane" is defined throughout this document as the sensor's dimensions in the x×y plane (see FIG. 1)) are approximately equal or less than the corresponding dimensions of the sensor. The circuitry is capable of delivering signals produced by the imaging sensor for further processing. The components of the imager, except for the imaging surface of the sensor and the objective lens system, are encapsulated by an isolating material. The electrical components of the circuitry are preferably lined-up behind the imaging sensor.

The imaging sensor can be a CCD or a CMOS sensor. If it is a CCD, it can be part of a Tape Automated Bonding (TAB) imager package.

The circuitry includes amplification, resistive, capacitance, and conductive components for electrically linking the components of the circuitry. The amplification component can be an amplifier. The resistive components can be embedded into the conducting wires used for linking the circuitry components. Preferably, burn-resistors are used. The electrical circuitry can further comprise a power source and a transmitter capable of wirelessly delivering the electrical signals produced by the circuitry and the imaging sensor to a remote location for processing. An internal power supply can be provided, making it unnecessary to provide power conductive wires to link the circuitry and the imaging sensor to an external power source. The circuitry may be an ASIC circuit and in a preferred embodiment the circuitry and the imaging sensor may be a single ASIC unit.

The imager components, the encapsulating material, and the transmission lines have heat resistant characteristics enabling the imager to remain undamaged and the quality of the images it produces to be essentially unaffected by repeated autoclaving procedures.

In another preferred embodiment, the imager assembly for a miniature camera head of the invention further comprising a plate, having dimensions in the plane parallel to the sensor plane equivalent to, or smaller than, the corresponding dimensions of the sensor. This plate is located beneath the sensor in an overlapping manner and includes grooves located at opposite edges at locations corresponding to the conductive leads. The circuitry is mounted on the bottom side of the plate and includes electrical connection points for electrically linking it to the sensor via the leads and also includes additional electrical connection points for connecting signal and power supply wires to deliver the amplified signal. The leads are connected to the connection points via the grooves such that the dimensions of the camera head in the plane parallel to the sensor plane are approximately equal to or less than the corresponding dimensions of the sensor. If the sensor is a CCD sensor that is part of a TAB imager package, then the protective strips of the TAB imager package can be bonded to the bottom side of the plate.

Another preferred embodiment of the imager assembly for a miniature camera head of the invention further comprises a second plate. The second plate has dimensions in the plane parallel to the sensor plane equivalent to or smaller than the corresponding dimensions of the sensor and is located in a parallel plane directly beneath the first plate in an overlapping manner. In this embodiment, the circuitry for driving the sensor and amplifying the electrical signals comprises two portions: a first portion, which is mounted on the bottom side of the first plate, and a second portion, which is mounted on the top side of the second plate. The first and the second portions face each other. The first portion includes electrical connection points for electrically linking it to the sensor via the leads and to the second portion via conductive wires linked to the second portion.

The plates can be PCBs. The PCBs can be made of ceramic or a special polymer material capable of withstanding high temperature and having a thermal expansion coefficient similar to that of the sensor.

The imager of the invention may further comprise electrical connection points situated on the bottom side of the second plate for connecting transmission lines to deliver the amplified signal. The second plate may further comprise bores for connecting electrical lines passing through them directly to the electrical connection points of the first circuitry portion located on the first plate. One portion of the circuitry may be mounted on the bottom side of the second plate and electrically linked to the other portion of the circuitry via conductive wires passing through bores in the second plate.

In another embodiment, the imager of the invention having two plates may further comprise one or more additional plates, each of which has dimensions in the plane parallel to the sensor plane equivalent to, or smaller than, the corresponding dimensions of the sensor. The additional plates are located in parallel planes directly beneath the second plate in an overlapping manner. Each of the additional plates comprises portions of the circuitry mounted on its top and/or bottom side and the portions of circuitry are electrically linked by transmission lines.

In another aspect, the present invention is directed towards an imaging system for processing and displaying the images that are acquired by the imager assembly of the invention. The system comprises:

a) a signal generator capable of providing voltage signals via the conductive wires for driving the imaging sensor to obtain acquisition rates of at least 100 fields per second;

b) circuitry for separately extracting each line of the acquired fields that are received from the imager;

c) circuitry for outputting a continuous display rate of at least 100 full-frames per second by combining the lines of the previously read field with the lines of the currently read fields; and d) a display system capable of displaying the outputted image in a continuous and non-interlaced mode, wherein the circuitry for extracting each line of the acquired fields separately prevents line summation during field readout thereby improving image quality and the dynamic response obtained by the imaging sensor.

According to the imaging system of the invention, the display system can be capable of displaying images in VGA synchronization standard.

In another aspect the present invention is directed towards a method for improving the image quality and the dynamic response obtained by a CCD imaging sensor. The method comprises:

a) providing voltage signals for driving the sensor to obtain an acquisition rate of at least 100 fields per second;

b) extracting each line of the acquired fields separately for preventing line summation during field readout;

c) outputting a continuous display rate of at least 100 full-frames per second by combining the lines of the previously read field with the lines of the currently read field; and d) displaying the outputted image in a continuous and non-interlaced mode.

According to the method of the invention, the images can be displayed utilizing VGA synchronization standard.

All the above and other characteristics and advantages of the invention will be further understood through the following illustrative and non-limitative description of preferred embodiments thereof, with reference to the appended drawings.

DETAILED DESCRIPTION OF PREFERRED EMBODIMENTS

Figure 1:
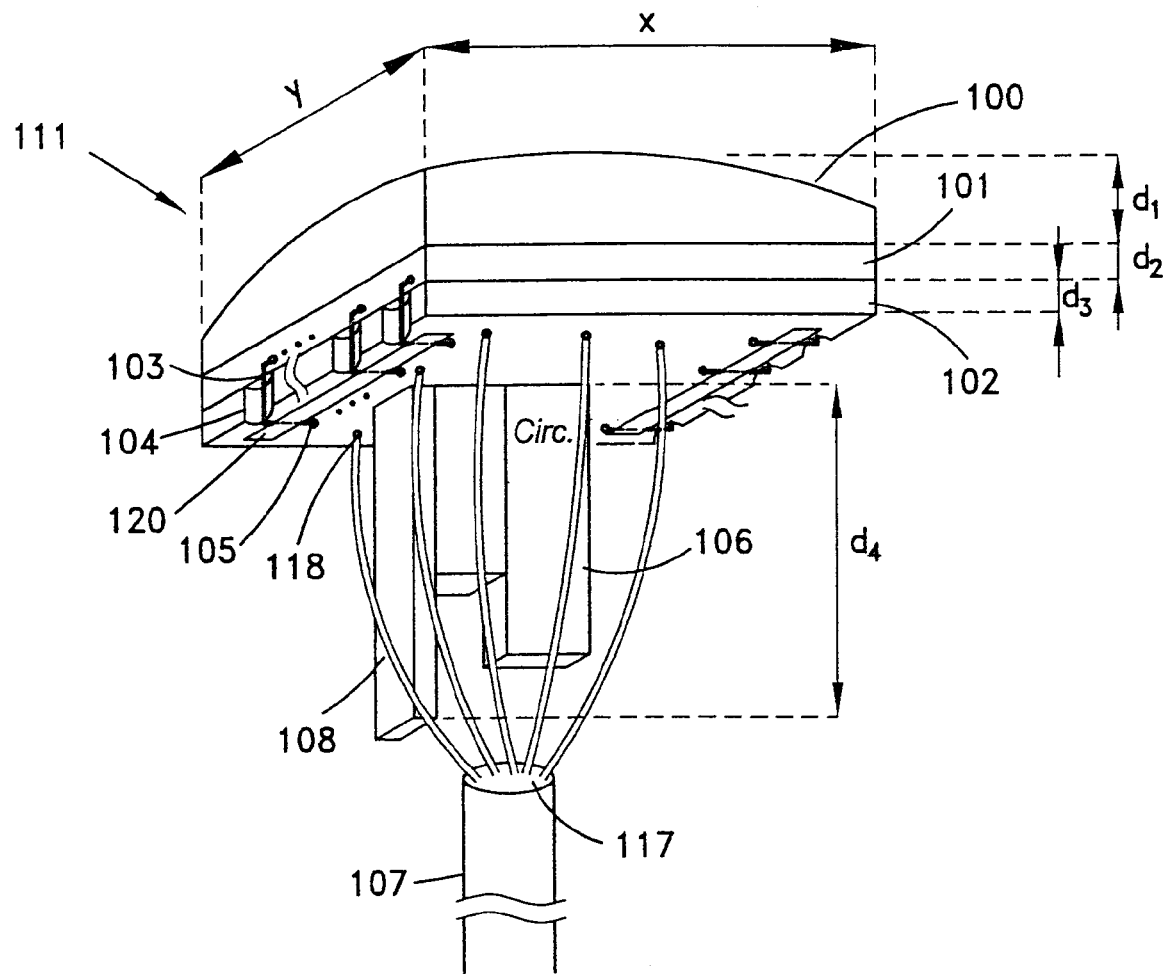
FIG. 1 illustrates an imager assembly utilizing a single parallel plate according to a preferred embodiment of the invention.

The present invention provides an autoclavable imager assembly, having minimal size, which functions as a miniature camera head. The camera head of the invention comprises an imaging sensor, such as CCD, to acquire the images and the components required to process and amplify the attained signals and to deliver them via conductive wires to a display system that digitally processes the attained signals. As explained hereinbelow, the quality of the image is greatly dependent on the number of electrical components that are mounted in the vicinity of the imager, to improve the signal quality. Electronic improvement is necessary because the signals that are transmitted via the conductive wires to the display system are distorted and attenuated by electrical noise and because of the presence of various other electrical effects, e.g., electrical resistance, along the conductive wires. The quality of the image also depends on many other factors including, but not limited to: the number of pixels in the imaging sensor, the amount of illumination (photon density) available, the amount of reflection from the target, environmental factors such as temperature of the cavity and residual temperature remaining in the camera head itself after the autoclaving process, and the activation procedure used for driving the imaging sensor.

There is a clear relationship between the physical dimensions of an instrument containing a miniature imaging-sensor having a certain number of pixels, and the amount of illumination needed to obtain a bright image. For example, a CCD with 480,000 pixels (⅛" CCD) requires a light source (xenon, halogen, LED, etc.) having a given intensity, while a smaller CCD (for example, a "1/10" CCD) with 300,000 pixels requires more light in order to present an image of similar quality. In the smaller-size CCD, the strength of the signals is less than for the larger CCD because the total number of photons received by the imaging sensor is substantially lower. A small size CCD can be made to have the same signal strength as a larger one by increasing the illumination intensity, however this will result in increasing the overall size of the imager. This is because increased intensity is achieved by adding illumination means (fibers, diodes, etc). Therefore, in order to achieve small packaging of the imager without increasing the illumination means, special electronics-related methods are required to increase the signal strength and quality. Thus the efforts to decrease the size of the imaging sensor require an increase in the number of components that need to be mounted near the imaging sensor in order to increase the gain and the resulting effect is an increase the overall volume of the package. This problem becomes more acute when the signal output from the CCD needs to travel along several meters of cable (for example, 5 to 15 meters) to the control processing unit without having any additional amplifiers between the attached CCD circuit and the control unit.

The present invention solves these problems and provides effective assembly designs that enable the provision of high quality, stable images having reduced noise; while, at the same time, achieving small packaging size by utilizing a minimal number of electronic components.

The main components required for delivering the image are an objective lens system (also referred to herein as an objective lens) located at the distal end of the imager assembly, an imaging sensor and a driver (amplifier) for operating the imaging sensor and delivering the image signals via the conductive wires.

FIG. 1 illustrates one preferred embodiment of an imager assembly 111 according to the invention. The components that are used to construct the imager 111 are assembled utilizing a layered configuration, in order to reduce the dimensions of the imager 111 to the minimum possible, namely the size defined by the sensor's dimensions in the sensor plane (referred to as the "sensor plane" throughout this application). The objective lens 100 is preferably of the same x×y dimensions as those of the sensor 101, or smaller, and is attached to the sensor's top (light receiving) face. The sensor 101 is attached to a horizontal plate 102, which is of the same x×y dimensions as those of the imaging sensor 101, or slightly smaller. As shown in FIG. 1, all the layers used to assemble the imager 111 are attached in parallel and are spatially aligned.

The electrical components (circuitry) 106 are mounted on the bottom surface of the horizontal plate 102. The electrical components 106 are connected to the imager leads 103 of the imaging sensor 101. The leads are vertically bent back towards the bottom surface of plate 102 via circular grooves 104 which are formed on opposite sides of the plate 102. The imager leads are linked to the circuitry 106 via connection points 105 located on the bottom surface of the horizontal plate 102, preferably by soldering. The signal transmission and electrical supply wires 108 of the cable 107 are also linked to the circuitry 106 via connection points 118 located on the bottom surface of the horizontal plate 102, which also serves as a PCB.

According to a preferred embodiment of the invention, the plate 102 is a ceramic PCB or special polymer (for example, Teflon) plate that withstands high temperature and has a thermo expansion coefficient similar to that of the sensor. The circuitry 106 is printed on the bottom surface of the plate. The circuitry 106 preferably includes an amplifying component (not shown), which is required for driving the imaging sensor 101. An N-channel field effect transistor (FET) is usually used as the amplifying element in such designs. In a preferred embodiment of the invention, the amplifying element is implemented by an amplifier circuit such as a Maxim operational amplifier that includes several amplifying stages. In order to reduce the physical dimensions of the circuitry 106, the resistive components (not shown) of the circuitry 106 are implemented by utilizing burn-resistors. The burn-resistors are embodied in the PCB conducting lines, and serve as electrical links between the electrical components. In this way the space consumed by the resistive components essentially becomes negligible. The space saved in this manner may be exploited either to reduce the amount of space consumed by the circuitry 106 or, alternatively, for introducing additional electrical components to improve the quality of the transmitted signal.

As shown in FIG. 1, the overall length of the imager 111 is the sum of the thicknesses/lengths of the various layers: d1 of the objective lens 100, d2 of the imaging sensor 101, d3 of the horizontal plate 102, and d4, the length of the electrical components 106. According to one preferred embodiment of the invention the thickness of the objective lens 100 is ~1.4 mm, the thickness of the imaging sensor 101 is ~0.65 mm, including the glass cover (e.g., Sony ICX257FKW or ICX256FKW CCD image sensors), the thickness of the plate 102 is preferably ~0.15 mm (it can be 0.08 mm or less), and the length of the gap d4 is preferably ~1.1 mm. The dimensions (x×y) of the imaging sensor (in the horizontal plate) are preferably ~2×2 mm, or smaller. The tips of the bent imager leads 103 add ~0.1 mm to the length in the x dimension of the imaging sensor 101, which results in dimensions in the sensor plane of the imager of about 2.2×2 mm, or less.

With this assembly, the overall dimensions of the imager 111 according to this preferred embodiment of the invention are about 2.2×2×3.3 mm. The imager assembly 111 is encapsulated by an isolating material, preferably non-conductive epoxy glue, which has a temperature resistance high enough to maintain the integrity of the imager 111 and its electronic components both in the operating environment and also under sterilizing conditions, for example, autoclave sterilization at 134° C. and pressure of 2.3 bar. The imaging sensor 101 is preferably a type of TAB CCD imager and, in this case, the protective strips 120 of the TAB imager packaging are preferably bonded to the bottom side of the horizontal plate 102.

Figure 2:
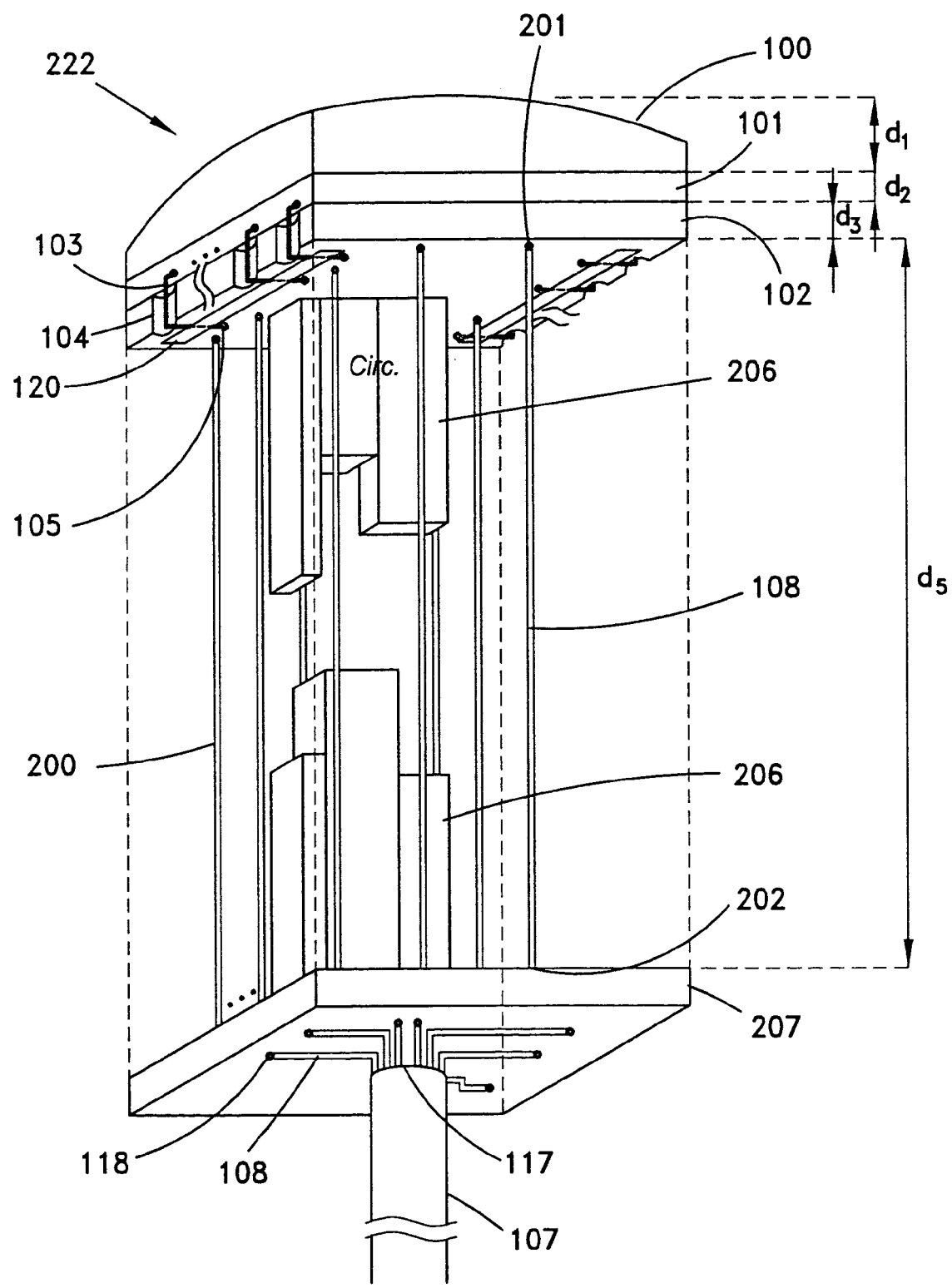
FIG. 2 illustrates an imager assembly utilizing a pair of parallel plates according to another preferred embodiment of the invention.
Figure 3A:
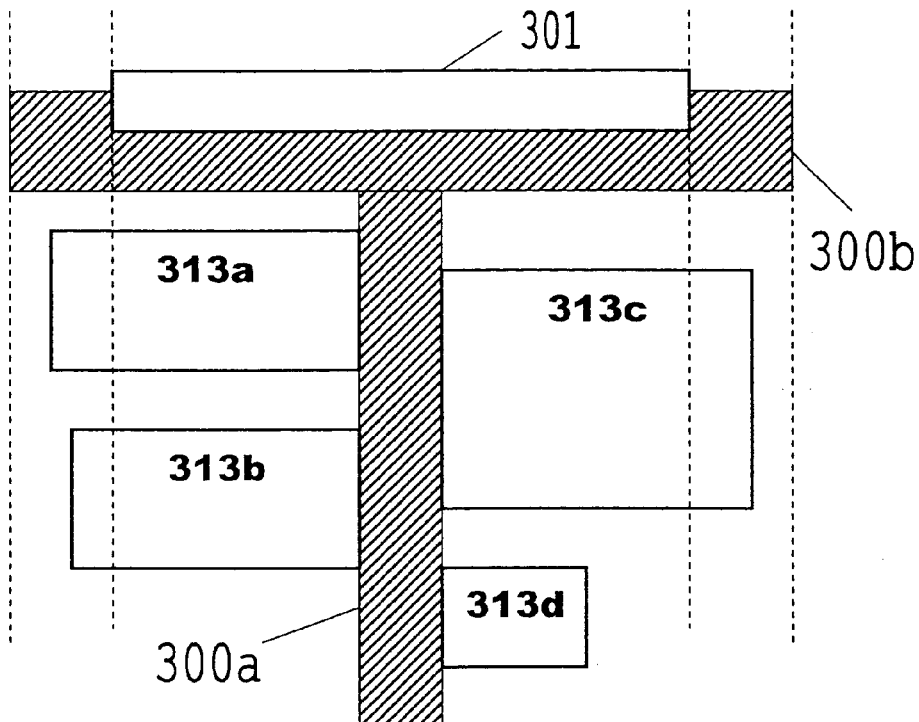
FIGS. 3A and 3B illustrate a side view of an imager assembly utilizing a T-shaped member support.
Figure 3B:
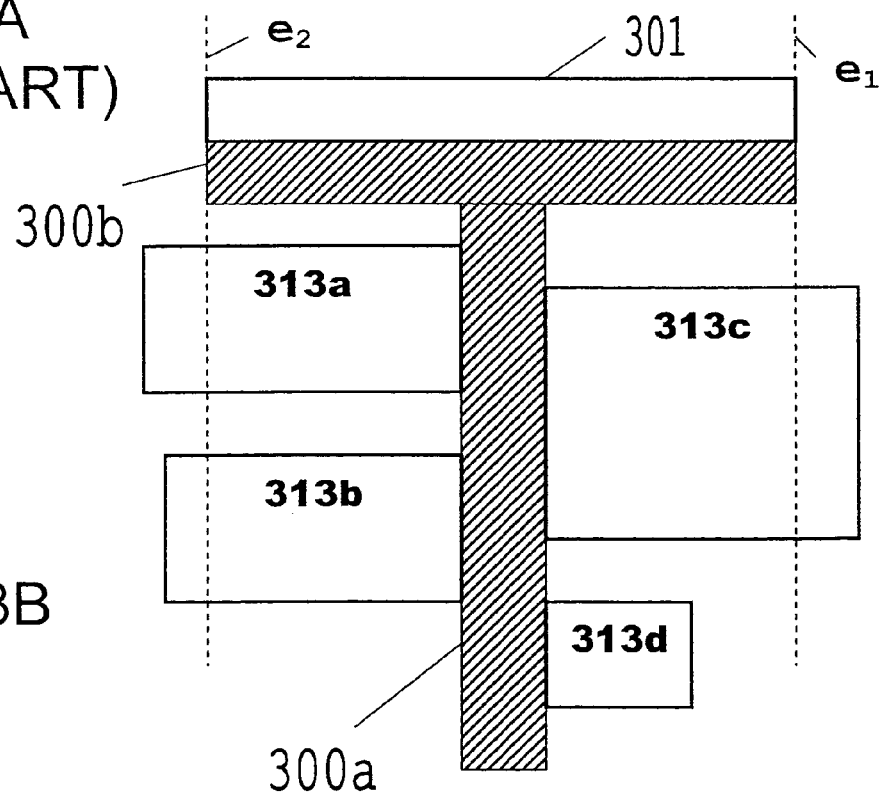
Figure 4A:
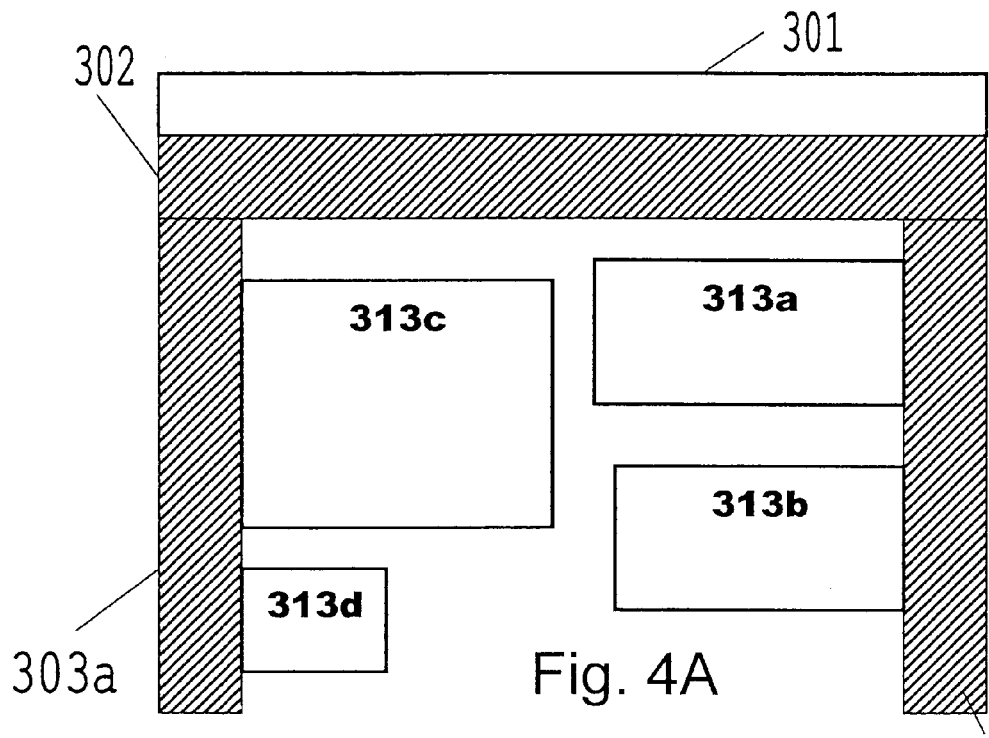
FIGS. 4A and 4B illustrate a side view of an imager assembly utilizing two vertical support members.
Figure 4B:
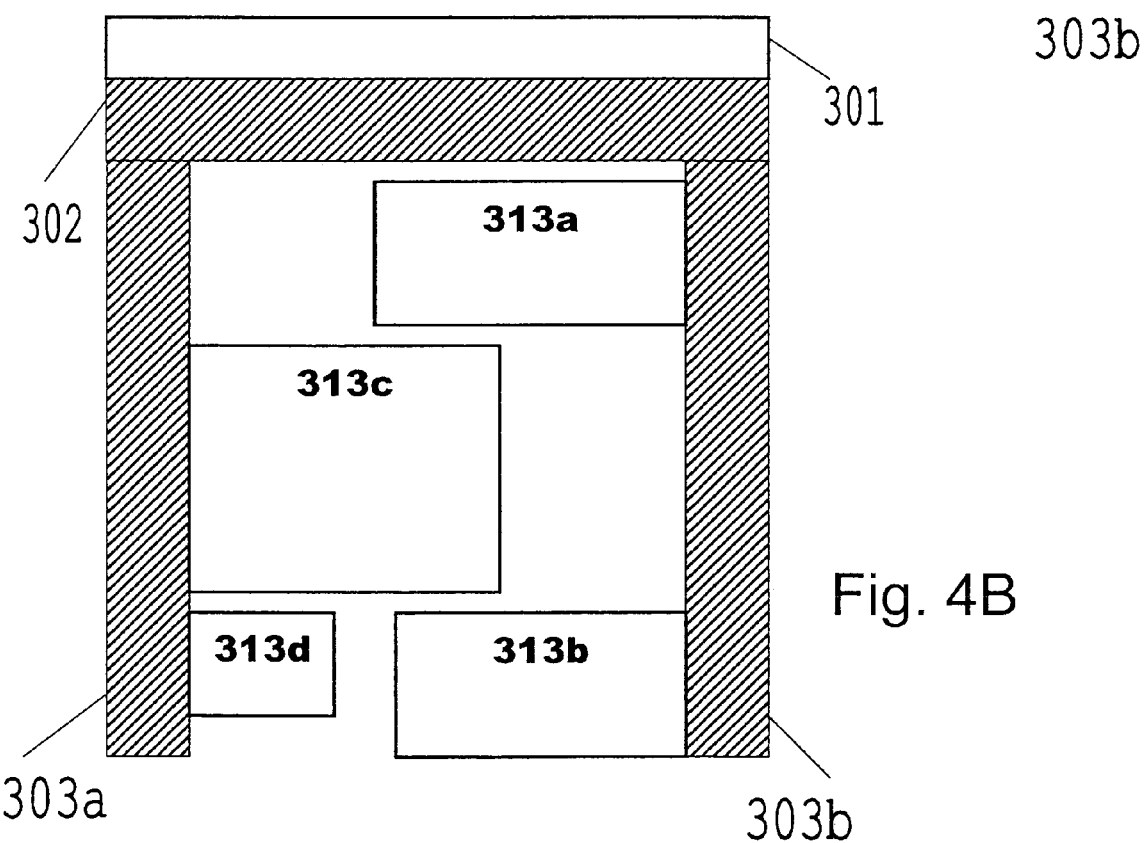

FIG. 2 illustrates another preferred embodiment of the invention wherein two parallel horizontal plates 102 and 207 are used for mounting the imaging sensor 101 and the electrical components 206. The imager assembly 222 shown in FIG. 2 is also arranged in a layered configuration. The objective lens 100 is attached to the imaging sensor 101. The imaging sensor is in turn, attached to the top surface of the first horizontal plate 102, which is of the same x×y dimensions as those of the imaging sensor 101, or slightly smaller. A second horizontal plate 207 is situated parallel to horizontal plate 102, forming a gap of length d5 with the first plate 102. The electronic circuitry 206 is connected to the imager leads 103, which are vertically bent back towards the bottom surface of the horizontal plate 102 via the circular grooves 104.

A portion of the electrical components (circuitry) 206 is mounted on the bottom surface of the first horizontal plate 102, and another portion of this circuitry 206 is mounted on the top surface of the second horizontal parallel plate 207. The transmission and electric supply wires 200 which are attached to contact points 201 on the bottom surface of the first horizontal plate 102, and to the contact points 202 on the top surface of the second parallel plate 207, are used to connect the two portions of circuitry 206. This preferred embodiment of the invention occupies a larger volume of space than the embodiment shown in FIG. 1, however the circuitry 206 used to drive the imaging sensor 101 can be designed to include more components than the corresponding circuit 106. The additional components are used to give this embodiment, for example, the ability to transmit both digital and analog signals over long distances (greater than five meters) or to transmit wireless signals.

The signal transmission and electrical supply wires 108 of the cable 107 are attached to the bottom surface of the second horizontal plate 207, and connected to the circuitry 206 via conduction paths 118 located within the second parallel plate 207. In this assembly, some of the wires 108 pass through bores in the second horizontal plate 207 and are directly linked to the imager leads 103 of the imaging sensor 101 and/or to the circuitry portion mounted on the first horizontal plate 102, via contact points 201.

The signal transmission and electrical supply wires 108 of the cable 107 are preferably bent vertically into the spatial plane of plate 207, such that they are attached to the bottom surface of the second horizontal plate 207 in their fully exposed length.

In this assembly the tip of the cable 117 is actually tightly attached to the second parallel plate 207, which further minimizes the length of the rigid portion of the imager 222 and reduces the rigid segment of the signal transmission and electrical supply wires 108 to a negligible length of about ~0.1 mm. Hence, the overall rigid length of the imager 222 is obtained by the summation of the thicknesses d1 (~1.4 mm) of the objective lens 100, d2 (~0.65 mm) of the imaging sensor 101, 2*d3 (~0.3 mm) of the first and second parallel plates 102 and 207, and d5 (~2.35 mm) of the distance between the parallel plates, thus obtaining physical dimensions of about ~2.2×2×4.7 mm.

It should be noted that additional plate layers can be added in parallel beneath the second horizontal plate 207, if required, according to the design needs. However, if additional plates are used, additional conductive wires 200 must be used to electrically link them, and the wires of the cable 107 will preferably be connected to the bottom surface of the last parallel plate and extend through bores in the plates towards the imager leads 103 of the imaging sensor 101. In such constructions electrical circuitry may be mounted on both sides of the additional parallel plates.

The circuitries 106, 206, of the preferred embodiments of the invention are preferably mounted on the horizontal plates utilizing state-of-the-art techniques. For example, the circuitry can be mounted by building the circuitry interconnections on the plates or by grooves and having its components (conductors, resistors, etc.) screen-printed onto the plates, utilizing various film technologies. The resistors (not shown) are preferably burn-resistors.

In the preferred embodiments of the invention the thickness of the ceramic plates (102 and 207) is preferably ~0.15 mm and can be even smaller, such as 0.08 mm, and the imager assemblies 111, 222 (with the exception of the objective lens and imaging sensor) are encapsulated by an isolating material with an appropriate thermal expansion coefficient (e.g., nonconductive epoxy glue, ceramic, or a polymer formula such as nonconductive Teflon, or PTFE). The imager components used preferably have temperature resistance to provide the imager with the ability to withstand sterilization temperatures achieved in procedures such as autoclaving. For instance, the imaging sensor can be from the Sony ICX257/6 family that are heat proof to ~155° C. and the ceramic plate used can be a Coors Ceramic Company AD-96 type which is heat proof to ~800° C. The encapsulation material is preferably heat proof to ~300° C. Capacitance elements are preferably types of VISHAY 100 nF, which are heat proof to ~210° C. The circuitry, which can be manufactured utilizing ceramic techniques, can have immunity to heat up to ~380° C., and the circuitry conducting paths are preferably made of gold. Several types of objective lens, such as KF9, which are heat proof to ~200° C., can be used. The signal transmission and power supply wires and cable are preferably able to withstand temperatures of at least ~210° C.

In the imager assemblies of the invention that were discussed heretofore an isolating material is preferably used to encapsulate the imager components. The encapsulating material provides sealing properties enabling the imager assembly to withstand repeated autoclaving procedures. The transparent adhesive used to attach the objective lens system to the CCD is capable of withstanding the autoclave temperature and has a thermal expansion coefficient that prevents temperature impacts, resulting from the autoclave temperature that may damage the imager construction.

Distortion of the imaging sensor signal may appear as a result of heating during the autoclaving process or as a result of working in a hot environment, such as a turbine engine. The two major types of distortions are of the spatial resolution and deviations from the Small Signal Approximation (around a working point), which is usually used to design the electronics. These distortions are minimized by utilizing electronic corrections, for instance doubling the acquiring image frequency, as will be discussed hereinbelow.

FIGS. 5A, 5B, 6A, and 6B illustrate imager assemblies (555 and 666) wherein the volume occupied by the imager is further reduced. These designs are preferably used for especially small imaging sensors (e.g., 2×2 mm or smaller). The general approach used in these designs is to mount the electrical circuitry 106 under the imaging sensor 101 without using plates (PCBs) as in the previously discussed embodiments. As in the previous embodiments, the imager leads 103 (and the protective strips 120, if a type of TAB imager packaging is used) are bent downwards in the vertical direction from the imaging sensor x×y plane. The components of the electrical circuitry 106 are connected directly according to the circuitry requirements, utilizing conductive wires 502, preferably by soldering and/or conductive glue and/or sonic soldering. As required by the circuit design, some of the transmission and electrical supply wires 108 are connected directly to the imager leads 103 and some of the wires 108 and the imager leads 103, may be connected directly to the electrical components of circuitry 106, preferably by soldering and/or conductive glue and/or sonic soldering.

All of the imager components except the objective lens system and the sensor's light receiving aperture are encapsulated utilizing an isolating material 500, preferably a type of a ceramic or non-conductive polymer material. The encapsulating material 500 is used to attach the electrical circuitry 106, the wires 108, and the imager leads 103 to the bottom side of the imaging sensor 101, and to provide the heat and pressure resistance required for protecting these components in autoclaving procedures. The dimensions of the imager are therefore reduced to the dimension of the imaging sensor (in the sensor plane), and the thickness of the lens d1, imaging sensor d2, and the length d5 of the encapsulated portion (in the direction perpendicular to the sensor plane), i.e. x×y×(d1+d2+d5)mm.

Figure 5A:
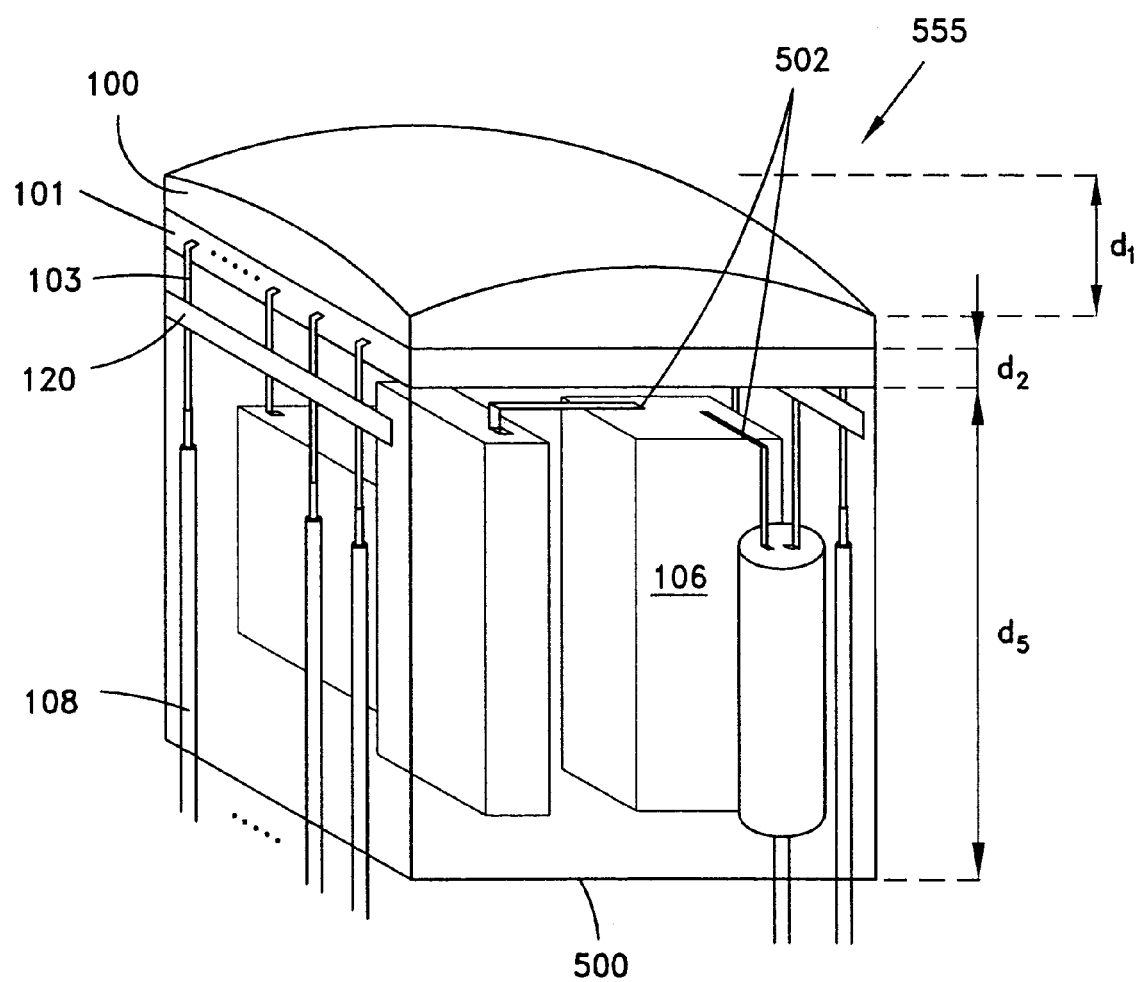
FIGS. 5A, 5B, 6A, and 6B illustrate imager assemblies of the invention in which the electrical circuitry is not mounted on PCBs.
Figure 5B:
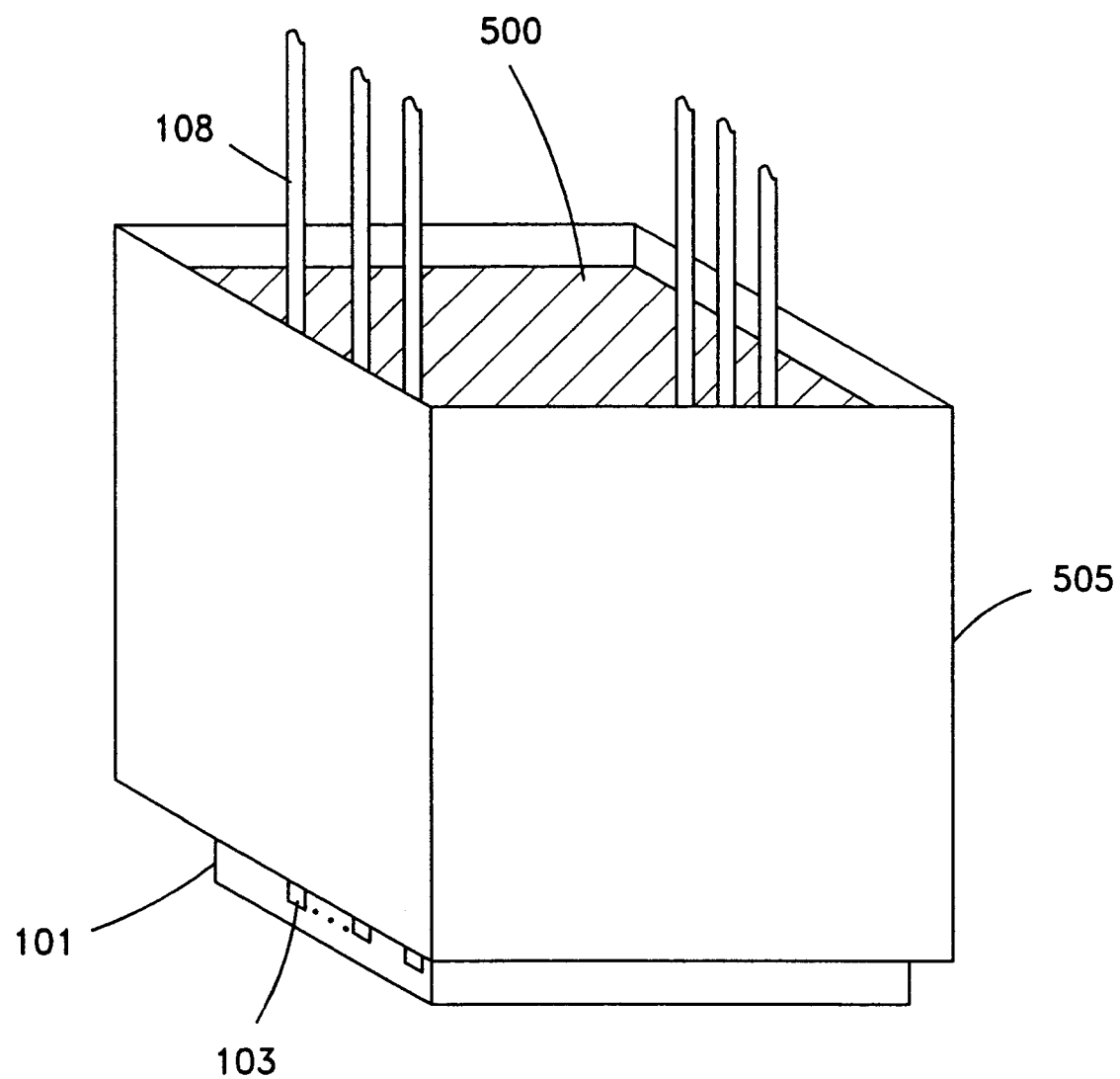

FIG. 5B demonstrates a possible way of encapsulating the imager assembly 555. A mold 505 is preferably used for molding the isolating material used for encapsulating the imager components. The mold is preferably a plastic mold (e.g., made of Teflon or similar material), which preferably has inner dimensions equivalent to the dimensions in the sensor plane of the imaging sensor 101, or slightly larger. The imager assembly is held inverted and the mold 505 is positioned on the bottom of the imaging sensor such that almost all the imager components are enclosed within the mold 505. The sensing surface of the imager is left outside the mold 505. The tips of the imager leads 103 can also be preferably enclosed in the mold. In this way all the internal components of the imager are enclosed within the mold 505, with the transmission and electrical supply wires 108 extending outside of the mold. The isolating material 500 is poured into the volume enclosed within the mold 505 and, once it hardens, the mold can be removed. After removal of the mold, the lens is attached to the sensing surface of the imager using a suitable transparent adhesive.

Figure 6A:
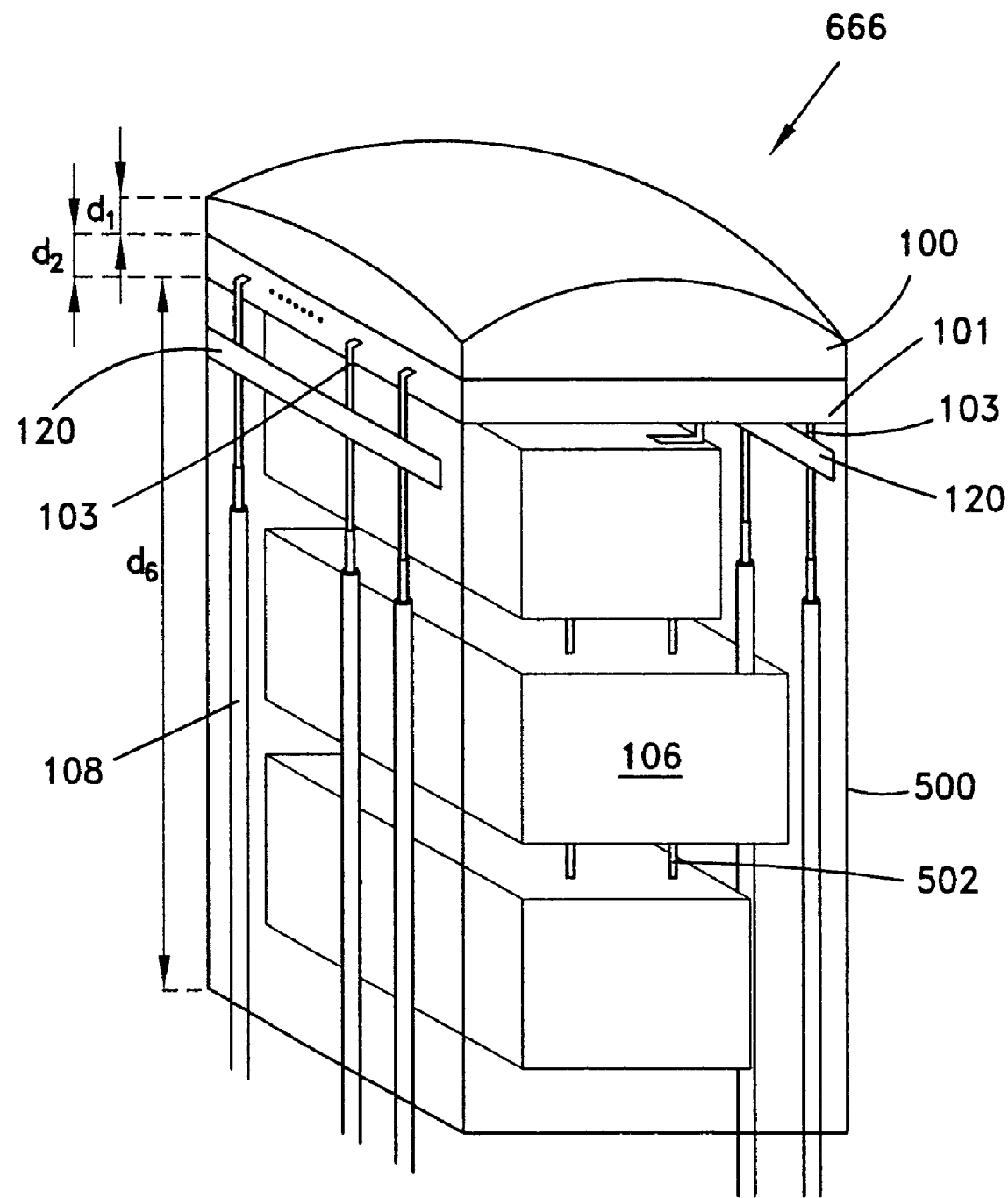

The imager assembly illustrated in FIG. 6A demonstrates another possible assembly, wherein all the electrical components of the circuitry 106 are placed in line, one after the other, behind the imaging sensor 101. This approach is particularly favorable in, but not limited to, implementations utilizing imaging sensors having physical dimensions of 1×1 mm, or smaller. This design is also advantageous in that it allows using electrical components which are larger in volume, but which are preferably not wider than the dimensions of the imaging sensor in the sensor plane. This approach affects the length of the imager, which may be elongated due to the lining of the imager inner components. However, this disadvantage can be alleviated by encapsulating the imager components utilizing a flexible isolating material (500). In this way the disadvantage of the elongated length of the imager 666 is eliminated, in particular when a very small imaging sensor is used, as intended in this design.

Figure 6B:
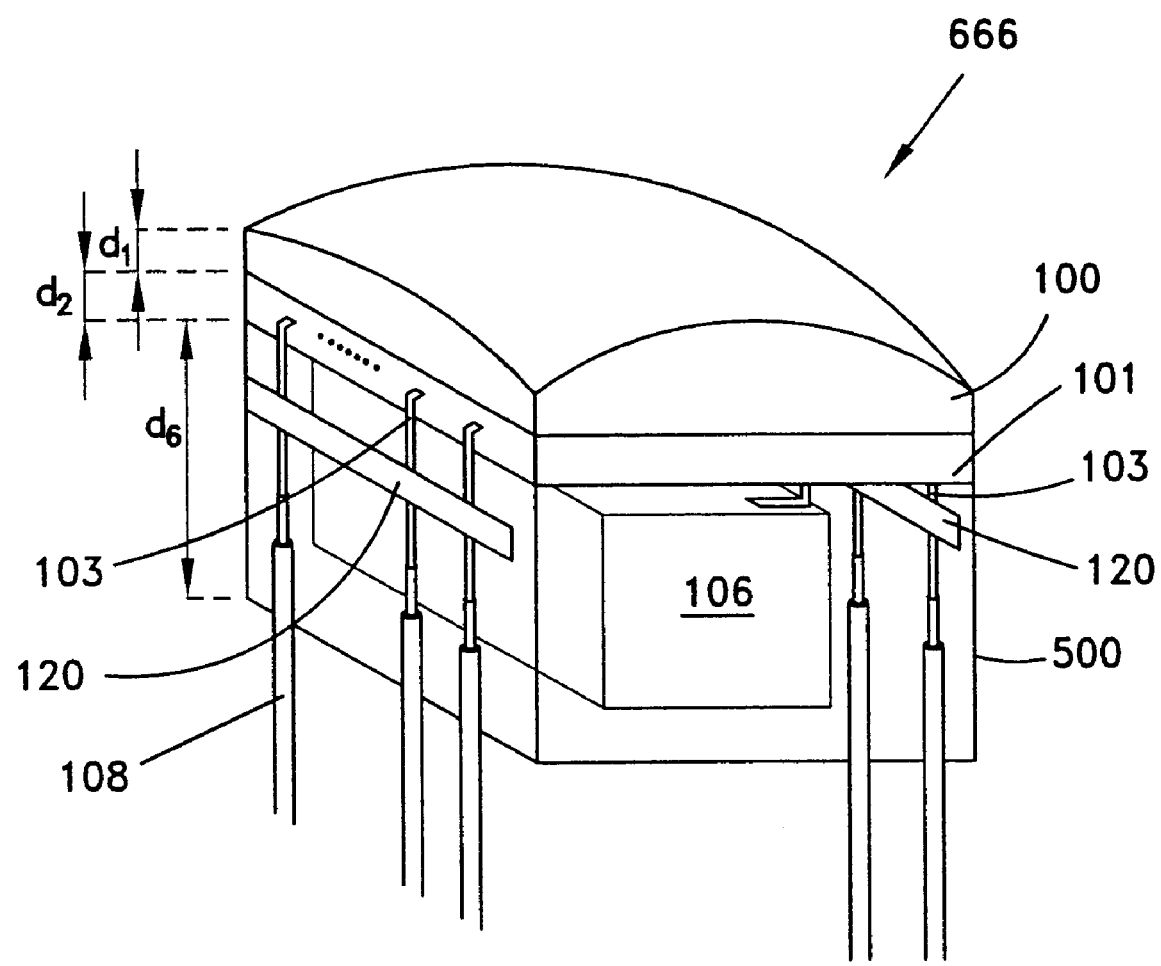

FIG. 6B shows an embodiment similar to that of FIG. 6A, but requiring less space. In the embodiment of FIG. 6B, all of the various circuit elements are incorporated into a single ASIC circuit 106. This embodiment can be even further reduced in size by incorporating the imaging sensor 101 and the electronic components of the circuitry 106 into a single ASIC unit.

Figure 7:
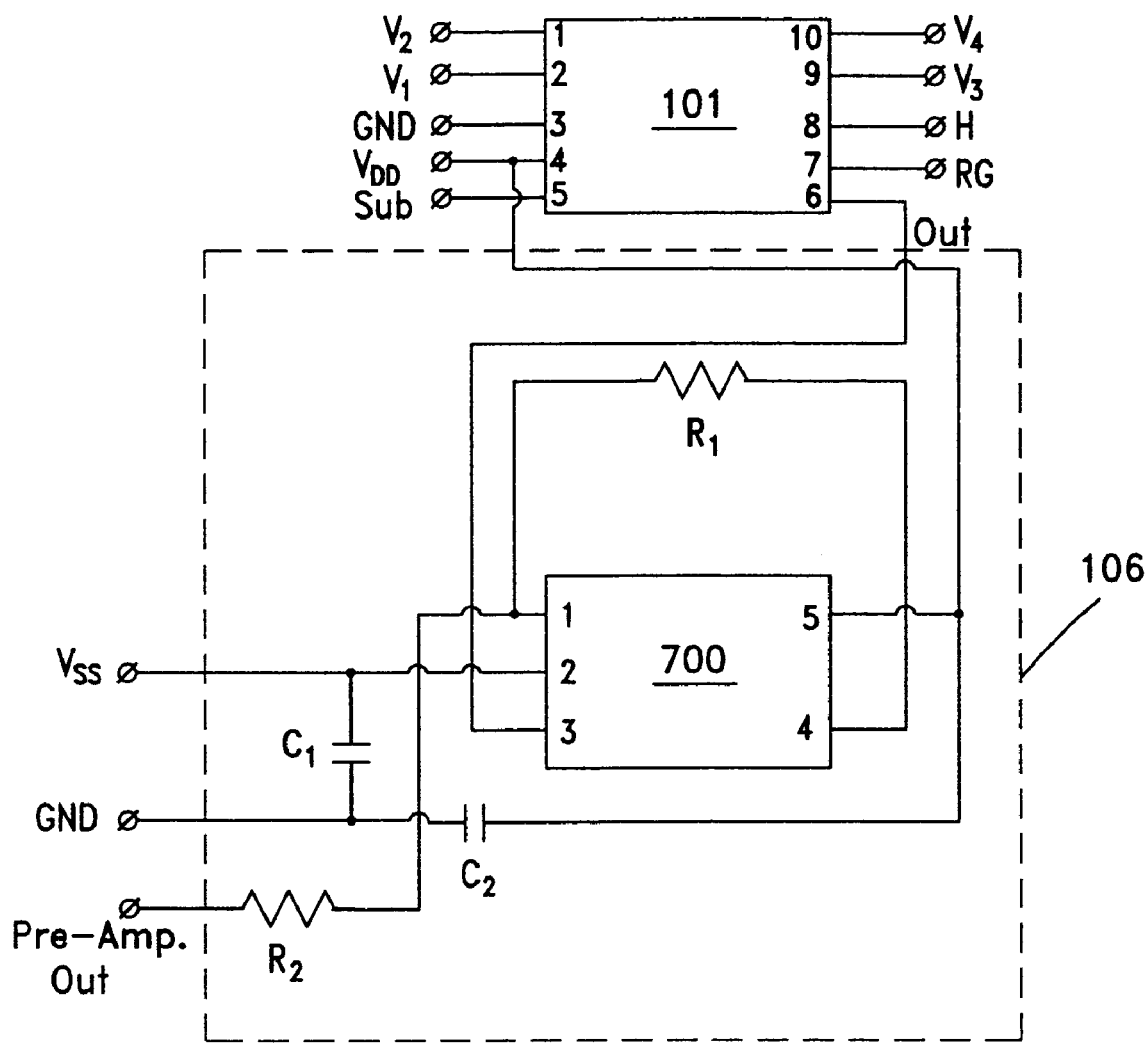
FIG. 7 schematically illustrates a preferred embodiment of the electrical circuitry of the invention.

FIG. 7 illustrates a possible embodiment of the circuitry 106 (206) of the invention. The imaging sensor is preferably a SONY ICX256/7FKW CCD (other cameras or CCDs that could be used are, for example, Panasonic camera GP-KS2MMH/ES1, based on 1/10" CCD and Sanyo LC99267FSB 1/8" CCD). The amplifier 700 is preferably a Maxim operational amplifier. The resistive components R1 and R2 are preferably a type of burn-resistor that are embedded into the conducting links (preferably gold wires) connecting the electrical components of the circuitry 106 (206), and which resistances are preferably 500 Ω and 50 Ω respectively. The capacitors C1 and C2 are both preferably 100 nF (25 v). The wires are industrial type 12-wire AWG #38 wires.

Throughout the above discussion, and in the drawings, the embodiments of the invention are described and illustrated as being linked by signal transmission and power supply wires. It should however be understood that the circuitries 106 and 206 can include an independent power supply and a radio transmitter for transmitting the image signals received by the circuitry. Obviously, in such wireless implementations there is no need to link the imager via transmission and power supply wires.

In the following discussion the method of operation of the imager is discussed with reference to FIGS. 8A-F. The imaging sensor is preferably a type of a CCD sensor and thus the discussion hereinbelow specifically relates to this type of sensor, and particularly to the SONY ICX256/7FKW CCD family.

Due to the miniaturization and the small number of pixels in a small-size imaging sensor (e.g., 1/10" CCD) versus the number in a larger sensor, there is a problem of electronic noise that reduces the quality of the image and diminishes the ability to transmit the signal over long distances, for example, over a 6-meter cable. In a typical 1/10" CCD for example there are 300,000 pixels, whereas in a typical 1/8" CCD there are 480,000 pixels. In order to solve the problems associated with the lower spatial resolution resulting from the reduced number of pixels and from the reduced level of illumination that result from the miniaturization, the operation of the CCD sensor is carried out as follows:

a. An acquisition rate from the CCD sensor of 100 fields (f1, f2, f3, . . . , f100) per second is performed, where each subsequently read field includes the output obtained from the even (e.g., $f_n = \{L^{(2)}_n, L^{(4)}_n, L^{(6)}_n, \ldots, L^{(m)}_n\}$) or odd (e.g., $f_{n-1} = \{L^{(1)}_{n-1}, L^{(3)}_{n-1}, L^{(5)}_{n-1}, \ldots, L^{(m-1)}_{n-1}\}$) cell lines of the sensor (where, n=1, 2, 3, . . . , 100 and m is an even integer).

b. Line summation during CCD readout is not performed (each line is separately extracted from the CCD) in order to retrieve the maximal resolution that the CCD sensor can provide.

c. An outputted on screen display rate of a continuous 100 full-frames per second (e.g., $\text{frame}^{(n)} = \{L^{(1)}_{n-1}, L^{(2)}_n, L^{(3)}_{n-1}, L^{(4)}_n, L^{(5)}_{n-1}, L^{(6)}_n, \ldots, L^{(m-1)}_{n-1}, L^{(m)}_n\}$) is obtained by continuously combining the lines of the previously retrieved field (e.g., $f_{n-1} = \{L^{(1)}_{n-1}, L^{(3)}_{n-1}, L^{(5)}_{n-1}, \ldots, L^{(m-1)}_{n-1}\}$) with the lines of the currently retrieved field (e.g., $f_n = \{L^{(2)}_n, L^{(4)}_n, L^{(6)}_n, \ldots, L^{(m)}_n\}$).

d. In order to display a continuous and stable image composed of the full-frame sequences, VGA synchronization standard is utilized.

By operating in this manner, the dynamic response of the CCD camera is significantly improved, in comparison with the PAL/NTSC standards, which are used in the majority of similar implementations. The preferred embodiment of the CCD camera is described hereinafter with reference to the PAL standard, although similar embodiments applying to the NTSC standard can also be used.

Figure 9A:
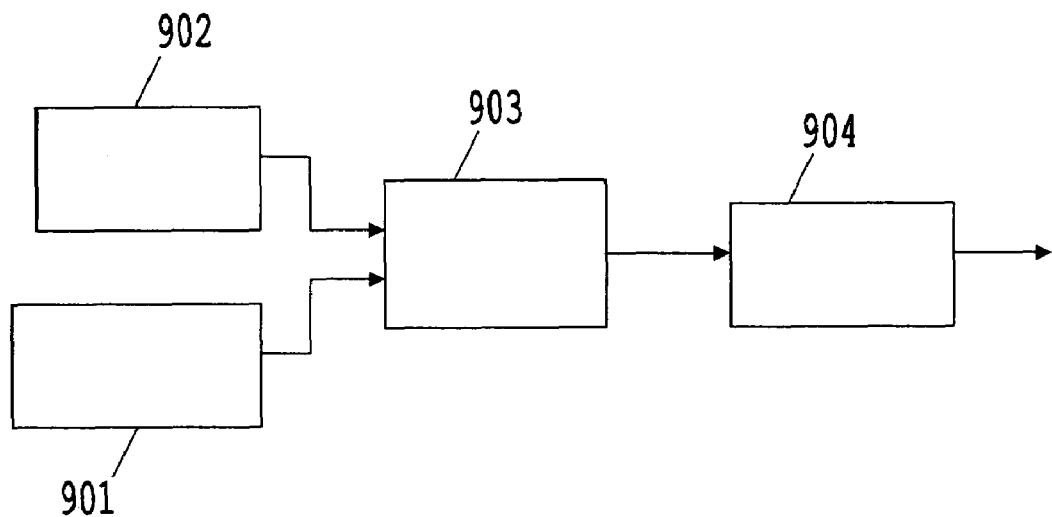
FIG. 9A is a block diagram illustrating a discrete analog horizontal phase drive.

The field acquisition rate is doubled, by increasing the pixel acquisition rate. This is preferably carried out by utilizing special discrete analog horizontal phase drivers and ultra fast analog signal processing circuits (e.g., double correlated sampling). FIG. 9A illustrates a possible implementation of a discrete analog horizontal phase driver that can be used to generate the signal required for operating the CCD sensor. A Wideband Phase Driver 903 is utilized for generating the signals, in accordance with the signals received from the Digital Generator 902 and the offsets provided via the Offset Adjustment 901. The Wideband Phase Driver 903 amplifies the generated signal and outputs it via the Bias Circuit 904, the output of which is used to for driving the CCD sensor. It should be noted that it is possible to use other signal multiplication means to increase the field rate.

Figure 9B:
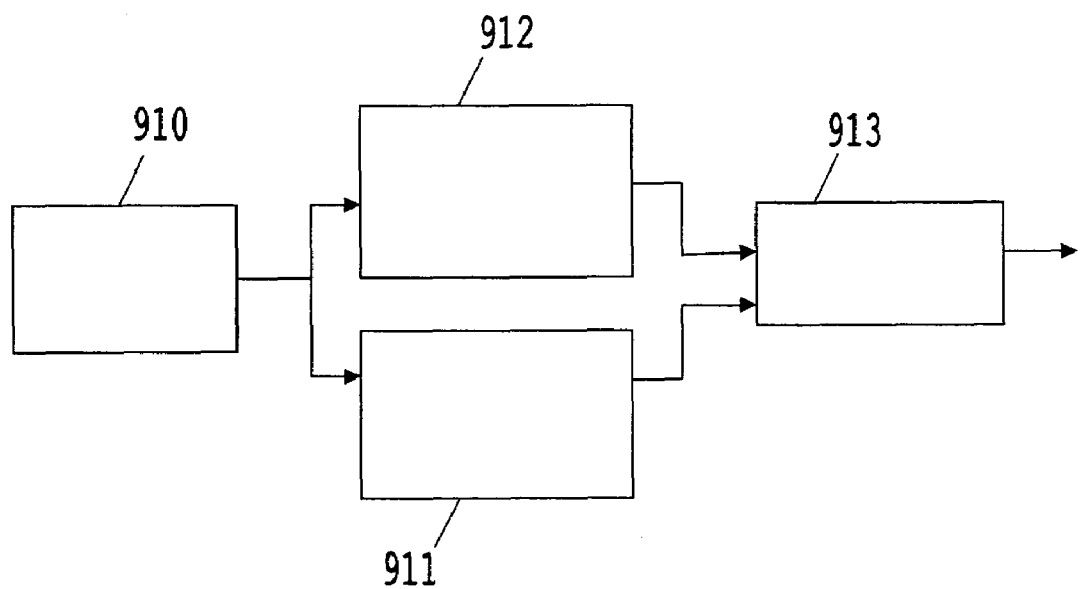
FIG. 9B is a block diagram illustrating an ultra fast analog signal processing circuitry.

FIG. 9B exemplifies a possible implementation of a double correlated sampler that can be used for the analog signal processing of the signal received from the imager. The output (FIG. 7) signal from Pre-amplifier 910 is fed into two Sample and Hold units, (Signal Sample & Hold unit 912 and Reference Level Sample & Hold unit 911), which are used to extract two signal levels of the outputted signal that are needed for determining a single pixel. The intensity of the acquired pixel is provided by the output of the Differential Stage 913, which provides the signal difference between the two signal levels provided by the Sample and Hold units, 911 and 912.

The VGA video standard is preferably used for the display, since it is capable of providing a frame refresh rate that is four times higher than that of the PAL standard. In addition, the outputted display is progressive, which improves the image provided and prevents flickering on the display screen.

The design of the vertical timing enables the separation between fields during the readout process. As exemplified in FIGS. 8A-F the voltage pattern V1-V4 is used to retrieve even and odd line fields (f1, f2, f3, . . . , f100). By providing these voltage patterns in high rates to the imaging sensor the quality and stability of the acquired image is substantially improved. This can be seen, for example, when comparing to the PAL/NTSC interlaced standards, in which 50 fields are acquired per second, where each field consists of half the number of lines actually available in the sensor, due to line summation.

The high voltage level (15 Volts) of the vertical phases, V1 and V3 (FIGS. 8B and 8D), that drives the CCD sensor, performs the readout process. The time difference between the high voltage levels of the waveforms of the "V1 and V3 Field Timing" (FIG. 8D), which is actually the time between two adjacent field readout processes, is 10 msec (i.e., a rate of 100 fields/sec is obtained).

Figure 8A:
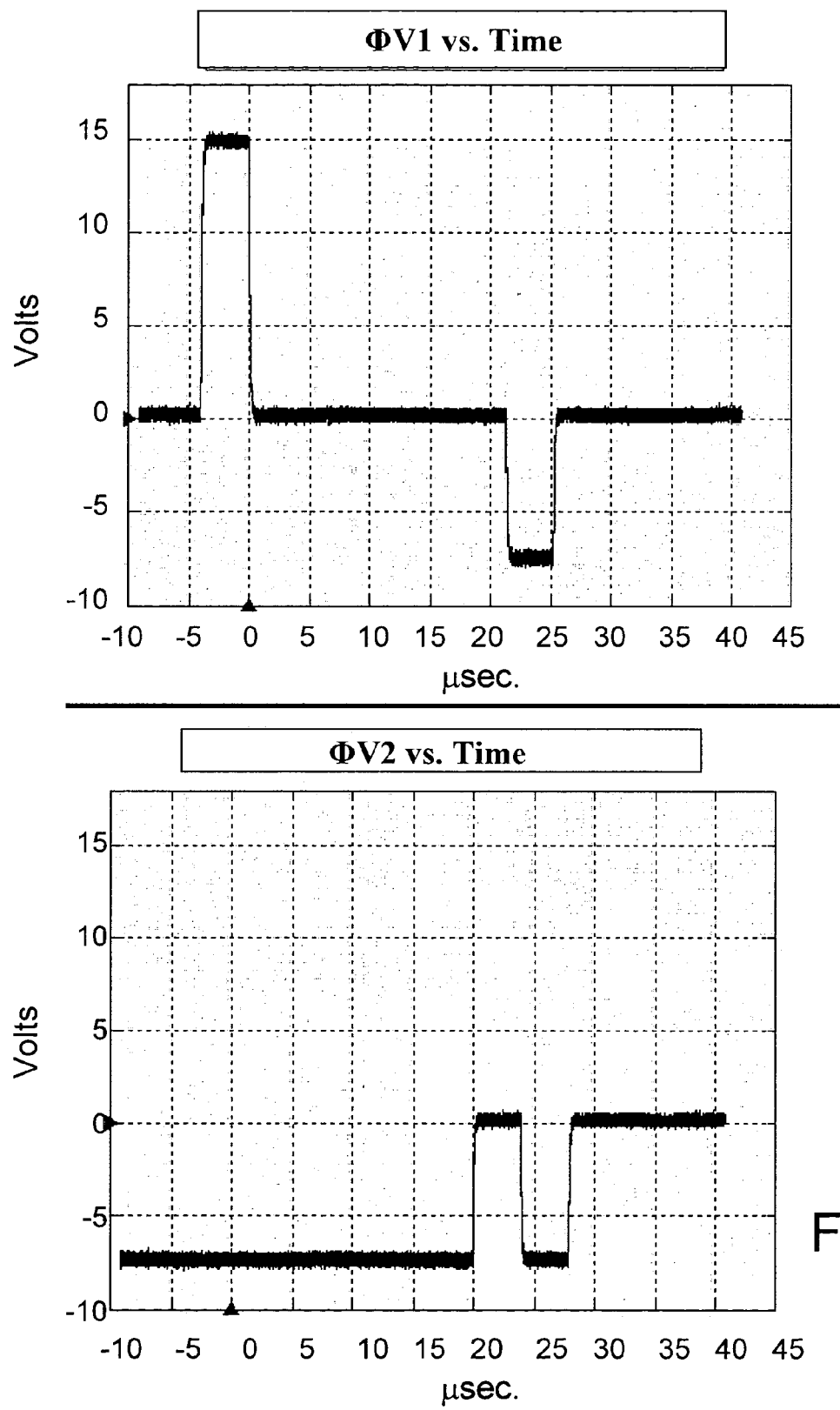
FIGS. 8A-8F are voltage graphs illustrating the electrical operation of the imager according to a preferred embodiment of the invention.
Figure 8B:
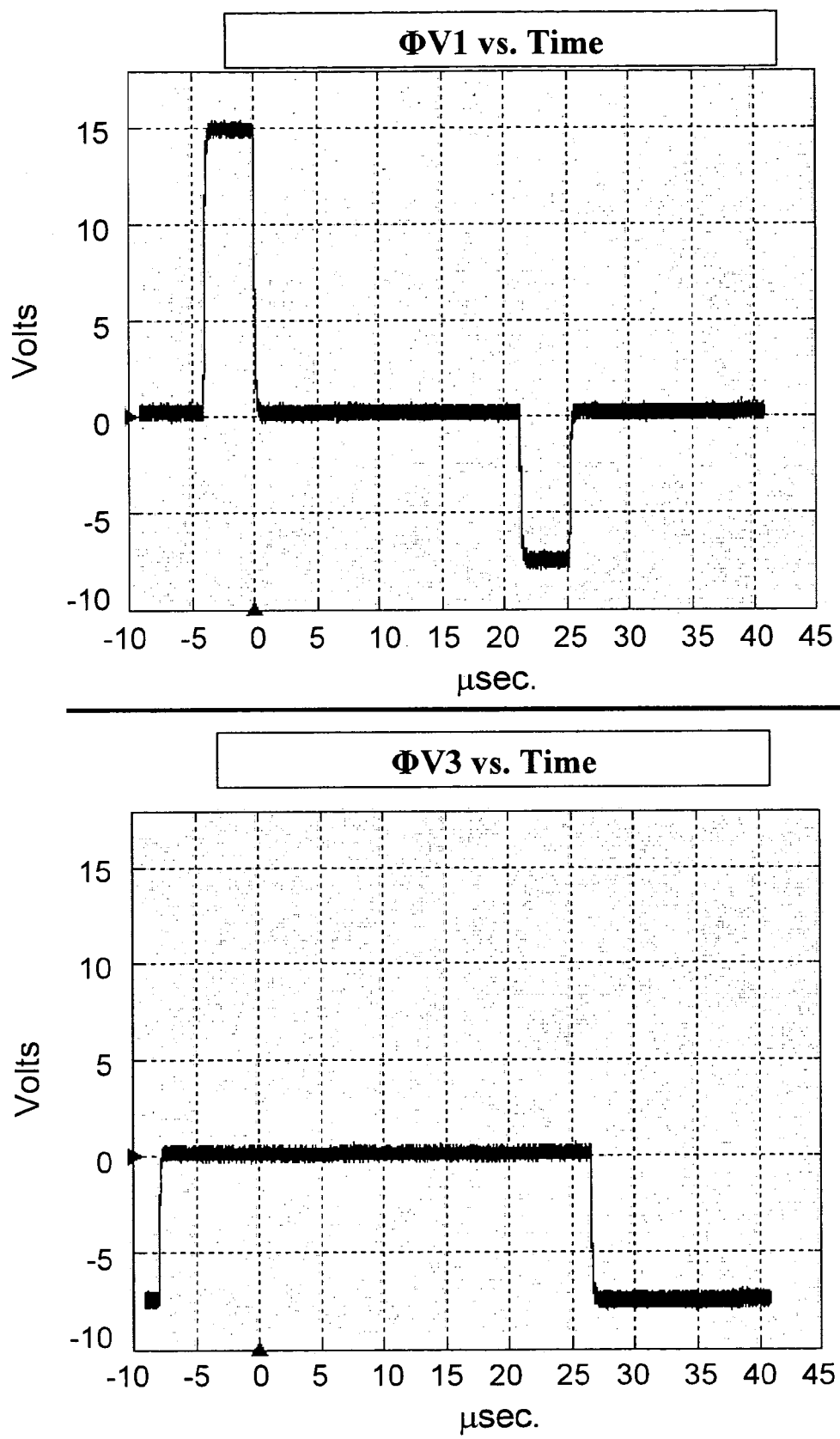
Figure 8C:
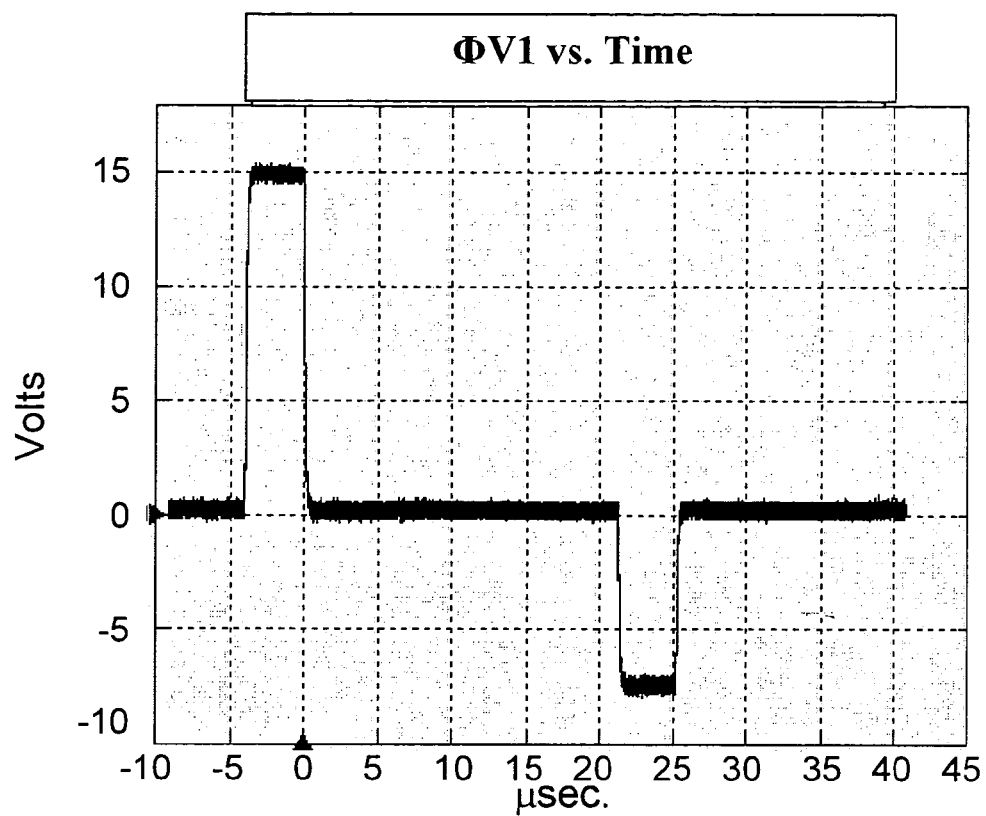
Figure 8C:
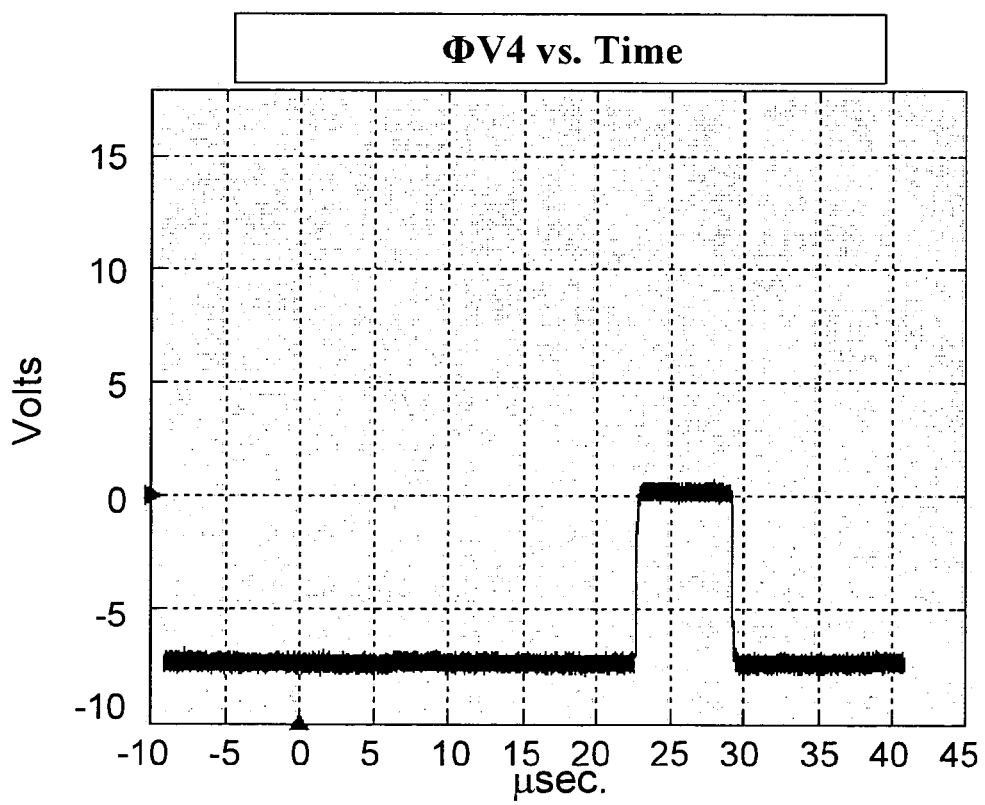
Figure 8D:
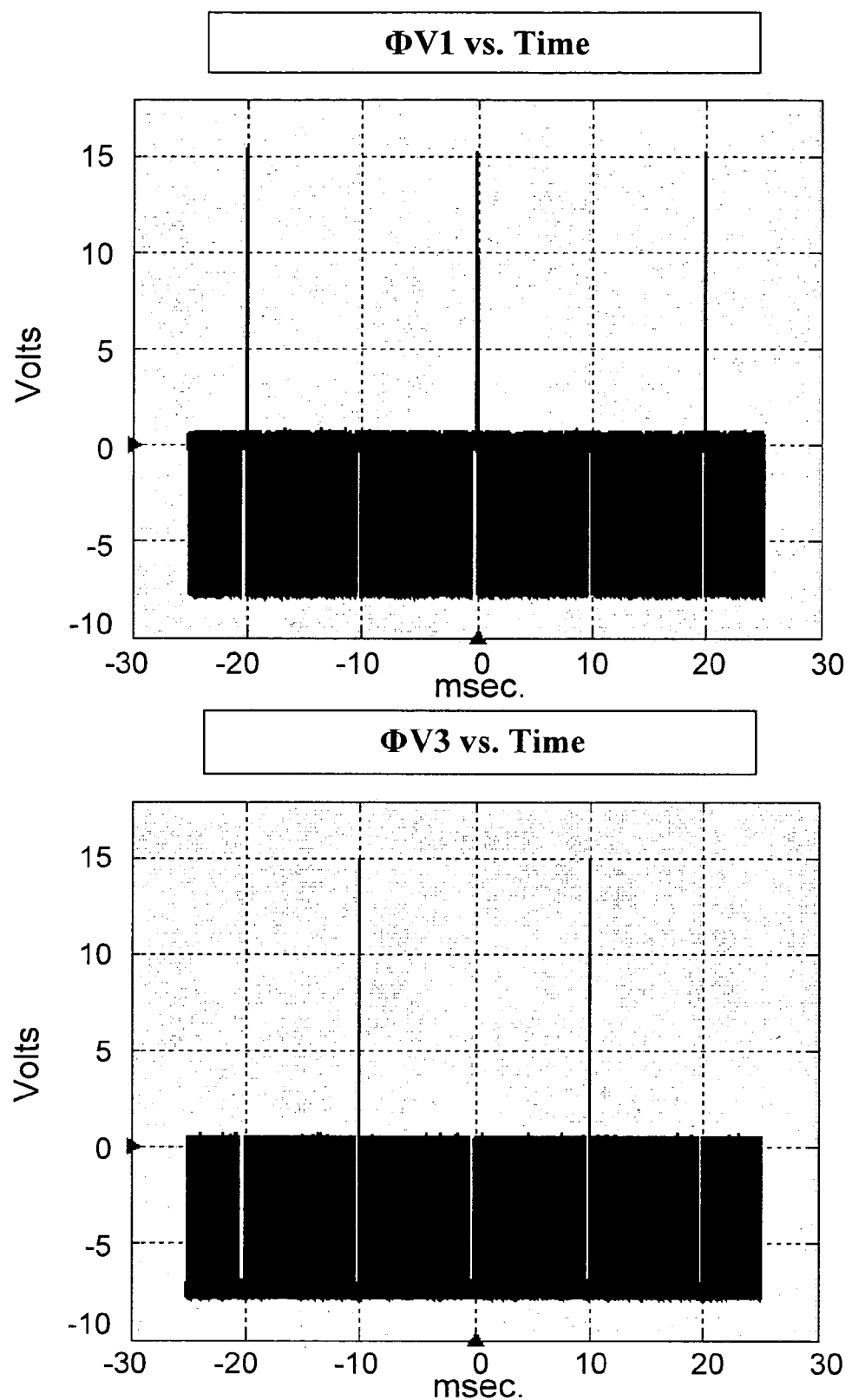

In addition, each field is extracted separately (only one phase appears in each field) as shown in FIG. 8D for V1 (odd field signal) and V3 (even field signal), thus field summation is not performed and the outputted image is actually made up of the full number of pixels that are practically available to the imaging sensor. The exact vertical timing of the readout process is illustrated for the odd field in waveforms "V1 and V2, Odd Field Readout" in FIG. 8A, "V1 and V3, Odd Field Readout" in FIG. 8B, and "V1 and V4, Odd Field Readout" in FIG. 8C.

As a result of doubling the field acquisition rate (versus that of the PAL standard), there is a need for a much higher pixel rate. FIG. 8F shows the waveform obtained on the "CCD's Output", which has a period of 40 nsec. Obviously, this output signal (25 M pixels/sec) is a substantial improvement over that obtained by use of the traditional PAL standard (9.5 M pixels/sec) for the spatial resolution of these CCDs.

Figure 8E:
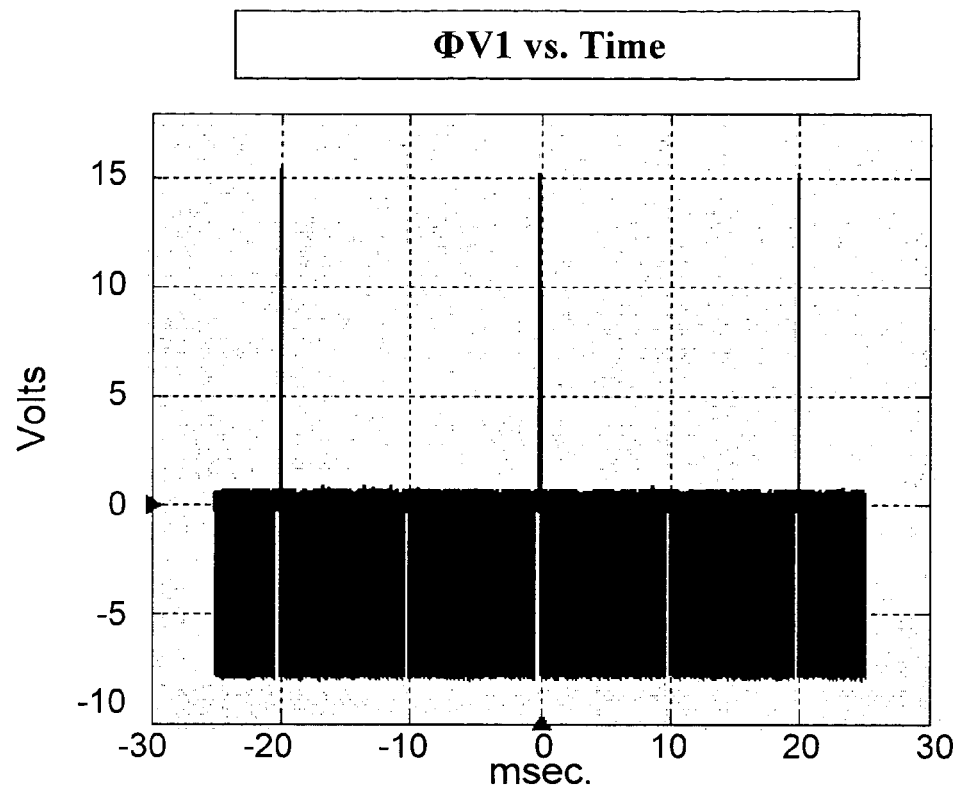
Figure 8E:
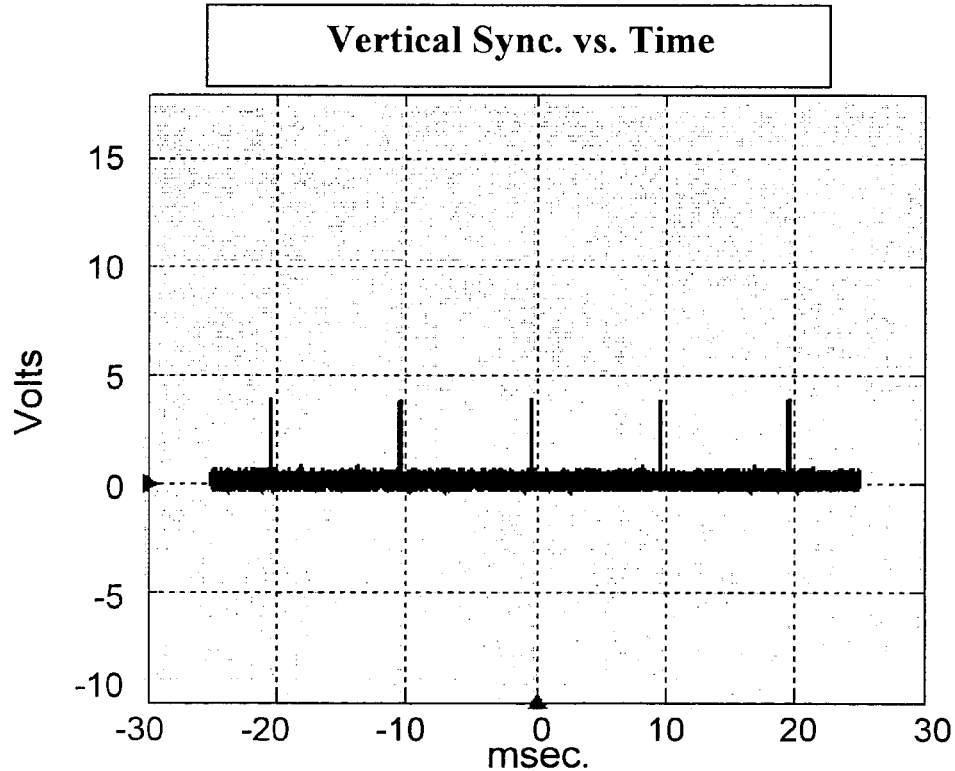
Figure 8F:
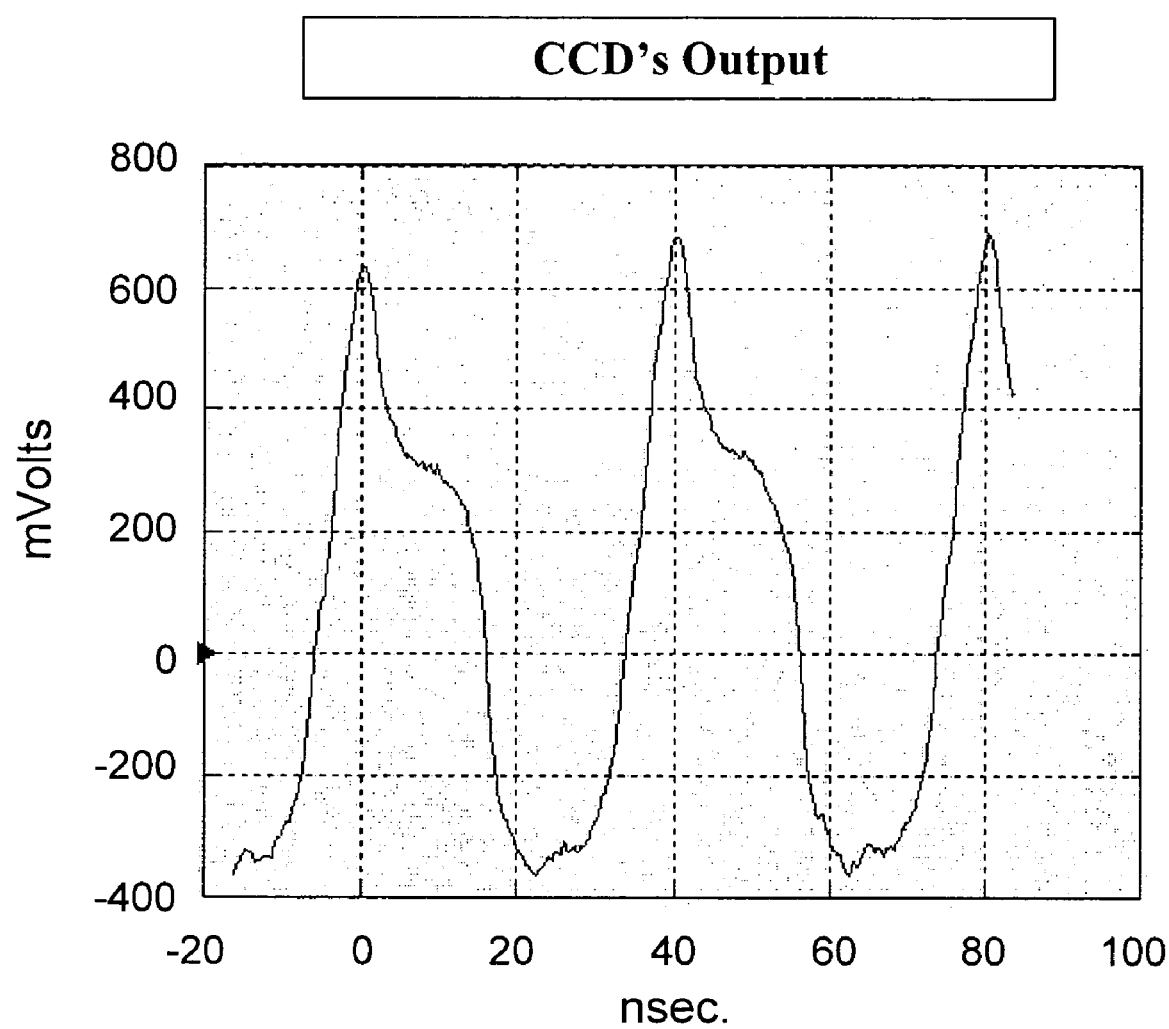

The vertical synchronization signal shown in FIG. 8E determines the display rate on screen. The time difference between two adjacent frame synchronizations signal (~4 volt pulse) is 10 msec (100 Hz).

In a preferred embodiment of the invention for each new field $f_n$ that the camera acquires, a new frame $\text{frame}^{(n)}$ is displayed on screen, in which the current field and the previously acquired field are combined (e.g., $\text{frame}^{(n)} = \{L^{(1)}_{n-1}, L^{(2)}_n, L^{(3)}_{n-1}, L^{(4)}_n, L^{(5)}_{n-1}, L^{(6)}_n, \ldots, L^{(m-1)}_{n-1}, L^{(m)}_n\}$).

It should be noted that it is possible to apply the same process for XGA or other display formats, *mutatis mutandis*.

The following table illustrates the main differences between the standard use of the above-mentioned CCD sensors and that of the invention.

TABLE 1

Video Solutions Based on ICX257FKW

| Feature | Standard use (PAL) | Nonstandard use (Present Invention) |
| --- | --- | --- |
| Acquisition Rate From CCD | 50 fields/sec | 100 fields/sec |
| Field Summation During CCD Readout | Exists (the CCD's output always contains the sum of 2 adjacent lines) | None (each line is separately extracted from the CCD) |
| Pixel Acquisition Rate | 9.5 M pixels/sec (For the current spatial resolution) | 25 M pixels/sec |
| Display Rate On Screen | 50 fields/sec | 100 fields/sec |
| Synchronization Standard on Screen | Y/C | VGA |
| Display Mode | Interlaced | Progressive |

We claim:

1. An imager assembly for a miniature camera head, comprising the following components:
   a) an imaging sensor having conductive leads emanating from two opposite sides of said sensor, for outputting and/or inputting electric signals and/or power;
   b) an objective lens system attached to the light receiving face of said sensor;
   c) circuitry, mounted beneath said imaging sensor, said circuitry adapted to drive said sensor, to amplify said electrical signals, and to deliver signals produced by said imaging sensor for further processing, where the components of said circuitry are electrically linked, according to the circuit requirements, to each other and to said sensor leads by conductive wires;
   d) conductive wires electrically linked to said circuitry and to the leads of the imaging sensor for conducting electrical signals between the electrical circuitry and a remote location; and
   e) conductive wires electrically linked to said circuitry and to said conductive leads of said imaging sensor to provide them with electrical power from an external power supply
      wherein: said conductive leads are bent, at least some of said wires for conducting electric signals and providing electrical power are connected directly to said conductive leads and directly to each other, and some of said conductive leads are connected directly to said electrical components of said circuitry without the use of a Printed Circuit Board (PCB), thereby allowing the dimensions in a plane parallel to the sensor plane of said camera head to be approximately equal to or less than the dimensions in the plane of said sensor.

2. An imager according to claim 1, wherein the electrical components of the circuitry are lined-up behind the imaging sensor.

3. An imager according to claim 1, wherein the imaging sensor is a CCD sensor.

4. An imager according to claim 3, wherein the CCD sensor is part of a TAB imager package.

5. An imager according to claim 1, wherein the imaging sensor is a CMOS sensor.

6. An imager according to claim 1, wherein the circuitry includes amplification, resistive, capacitance, and conductive components for electrically linking the components of said circuitry.

7. An imager according to claim 6, wherein the amplification component is an amplifier.

8. An imager according to claim 6, wherein the resistive components are embedded into the conducting wires used for linking the circuitry components.

9. An imager according to claim 8, wherein the resistive components are burn-resistors.

10. An imager according to claim 6, wherein the capacitance components are embedded into the conducting wires used for linking the circuitry components.

11. An imager according to claim 1, wherein the electrical circuitry further comprises a power source and a transmitter capable of wirelessly delivering the electrical signals produced by said circuitry and the imaging sensor to a remote location for processing.

12. An imager according to claim 1, further comprising a power supply wherein the circuitry and the imaging sensor are not linked by power supply wires to an external power source.

13. An imager according to claim 1 wherein the imager components, the encapsulating material, and the conducting wires have heat resistant characteristics enabling said imager to remain undamaged and the quality of the images it produces to be essentially unaffected by repeated autoclaving procedures.

14. An imager according to claim 1, wherein the circuitry comprises an ASIC circuit.

15. An imager according to claim 1, wherein the circuitry and imaging sensor comprise a single ASIC unit.

16. An imager assembly for a miniature camera head according to claim 1, further comprising a plate, having dimensions in the plane parallel to the sensor plane that are equivalent to, or smaller than, the corresponding dimensions of the sensor and located beneath said sensor in an overlapping manner,
    wherein said plate includes grooves located at opposite edges at locations corresponding to the conductive leads; the circuitry is mounted on the bottom side of said plate; said circuitry includes electrical connection points for electrically linking it to said sensor via said leads and additional electrical connection points for connecting transmission and power supply wires to deliver the amplified signal; and said leads are connected to said connection points via said grooves such that the dimensions of said camera head in the plane parallel to the sensor plane are approximately equal to or less than the corresponding dimensions of said sensor.

17. An imager according to claim 16, wherein the CCD sensor is part of a TAB imager package and the protective strips of said TAB imager package are bonded to the bottom side of the plate.

18. An imager assembly for a miniature camera head according to claim 16, further comprising a second plate, having dimensions in the plane parallel to the sensor plane approximately equal to, or smaller than, the corresponding dimensions of the sensor and located in a parallel plane directly beneath the first plate in an overlapping manner,
    wherein the circuitry for driving said sensor and amplifying said electrical signals comprises two portions, a first portion which is mounted on the bottom side of the first plate and a second portion which is mounted on the top side of said second plate such that said first and said second portions face each other and said first portion includes electrical connection points for electrically linking it to said sensor via said leads and to said second portion via conductive wires linked to said second portion.

19. An imager according to claim 16, wherein the plate is a Printed Circuit Board (PCB).

20. An imager according to claim 19, wherein the PCB is made of ceramic or a special polymer material, withstands high temperature, and has a thermal expansion coefficient similar to that of the sensor.

21. An imager according to claim 18, further comprising electrical connection points situated on the bottom side of the second plate for connecting transmission lines to deliver the amplified signal.

22. An imager according to claim 18, wherein the second plate further comprises bores for connecting transmission lines passing through said bores directly to the electrical connection points of the first circuitry portion located on the first plate.

23. An imager according to claim 18, wherein one portion of the circuitry is mounted on the bottom side of the second plate and electrically linked to the other portion of said circuitry via conductive wires passing through bores in said second plate.

24. An imager according to claim 18, further comprising one or more additional plates, each of which having dimensions in the plane parallel to the sensor plane approximately equal to, or smaller than, the corresponding dimensions of said sensor, and located in parallel planes directly beneath the second plate in an overlapping manner, wherein each of said additional plates comprise portions of the circuitry mounted on the top and/or the bottom side of said additional plates said portions of circuitry being electrically linked by transmission lines.

25. An imager according to claim 18, wherein the plate is a Printed Circuit Board (PCB).

26. An imager according to claim 25, wherein the PCB is made of ceramic or a special polymer material, withstands high temperature, and has a thermal expansion coefficient similar to that of the sensor.

27. An imager according to claim 1, wherein the components of said imager, except for the imaging surface of the sensor and the objective lens system, are encapsulated by an isolating material.

28. An imager according to claim 1, wherein all of the wires for conducting electric signals and providing electrical power are connected directly to the conductive leads and directly to each other, and wherein all of the conductive leads are connected directly to the electrical components of the circuitry, without the use of a PCB.

29. An imaging system for processing and displaying images comprising
   a) an imager according to claim 1.
   b) a signal generator capable of providing voltage signals via the conductive wires for driving the imager to obtain acquisition rates of at least 100 fields per second;
   c) circuitry for separately extracting eachl line of the acquired fields that are received from the imager;
   d) circuitry for outputting a continuous display rate of at least 100 full-frames per second by combining the lines of the previously read field with the lines of the currently read fields; and
   f) a display system capable of displaying the outputted image in a continuous and non-interlaced mode, wherein the circuitry for extracting each line of the acquired fields separately prevents line summation during field readout thereby improving image quality and the dynamic response obtained by the imager.

30. An imaging system according to claim 29, wherein the display system is capable of displaying images in VGA synchronization standard.

\* \* \* \* \*